(12) United States Patent
Ram

(10) Patent No.: US 10,932,684 B2
(45) Date of Patent: **\*Mar. 2, 2021**

(54) MICROELECTRONIC SENSOR FOR AIR QUALITY MONITORING

(71) Applicant: EPITRONIC HOLDINGS PTE LTD., Singapore (SG)

(72) Inventor: Ayal Ram, Singapore (SG)

(73) Assignee: EPITRONIC HOLDINGS PTE LTD., Singapore (SG)

( \* ) Notice: Subject to any disclaimer, the term of this patent is extended or adjusted under 35 U.S.C. 154(b) by 358 days.

This patent is subject to a terminal disclaimer.

(21) Appl. No.: 16/122,265

(22) Filed: Sep. 5, 2018

(65) Prior Publication Data

US 2019/0021623 A1   Jan. 24, 2019

Related U.S. Application Data

(63) Continuation-in-part of application No. PCT/IB2017/051325, filed on Mar. 7, 2017, which is
(Continued)

(51) Int. Cl.
*H01L 29/778* (2006.01)
*A61B 5/0408* (2006.01)
(Continued)

(52) U.S. Cl.
CPC .......... *A61B 5/0408* (2013.01); *A61B 1/2736* (2013.01); *A61B 3/16* (2013.01);
(Continued)

(58) Field of Classification Search
CPC . H01L 29/2003; H01L 27/20; H01L 29/7783; H01L 29/66462; H01L 27/14806;
(Continued)

(56) References Cited

U.S. PATENT DOCUMENTS 8,896,025 B2 \* 11/2014 Koyama ........... H01L 21/30621
257/190
2002/0185655 A1 \* 12/2002 Fahimulla ............ B82Y 10/00
257/192
(Continued)

OTHER PUBLICATIONS

Offermans et al; "Suspended AlGaN/GaN membrane devices with recessed open gate areas for ultra-low-power air quality monitoring" 2015 IEEE International Electron Devices Meeting (IEDM). Dec. 7, 2015, pp. 33.6.1-33.6.4.
(Continued)

*Primary Examiner* — Joseph A Stoklosa
*Assistant Examiner* — Brian M Antiskay
(74) *Attorney, Agent, or Firm* — The Roy Gross Law Firm, LLC; Roy Gross

(57) ABSTRACT

In some embodiments, a microelectronic sensor includes an open-gate pseudo-conductive high-electron mobility transistor and used for air quality monitoring. The transistor comprises a substrate, on which a multilayer hetero-junction structure is deposited. This hetero-junction structure comprises a buffer layer and a barrier layer, both grown from III-V single-crystalline or polycrystalline semiconductor materials. A two-dimensional electron gas (2DEG) conducting channel is formed at the interface between the buffer and barrier layers and provides electron current in the system between source and drain electrodes. The source and drain contacts are non-ohmic (capacitively-coupled) and connected to the formed 2DEG channel and to the electrical metallizations, the latter are placed on top of the transistor and connect it to the sensor system. The metal gate electrode is placed between the source and drain areas on or above the barrier layer, which may be recessed or grown to a specific thickness. An optional dielectric layer is deposited on top of the barrier layer.

19 Claims, 24 Drawing Sheets
(21 of 24 Drawing Sheet(s) Filed in Color)

Related U.S. Application Data a continuation of application No. 15/067,093, filed on Mar. 10, 2016, now abandoned, and a continuation of application No. 15/157,285, filed on May 17, 2016, now abandoned.

(60) Provisional application No. 62/362,167, filed on Jul. 14, 2016.

(51) Int. Cl.
| | |
|---|---|
| *H01L 29/205* | (2006.01) |
| *A61B 5/00* | (2006.01) |
| *A61B 5/04* | (2006.01) |
| *A61B 5/11* | (2006.01) |
| *A61B 5/0452* | (2006.01) |
| *A61B 3/16* | (2006.01) |
| *A61B 1/273* | (2006.01) |
| *A61B 5/0478* | (2006.01) |
| *A61B 7/04* | (2006.01) |
| *A61B 5/021* | (2006.01) |
| *G01N 27/12* | (2006.01) |
| *G01N 33/00* | (2006.01) |
| *A61B 5/08* | (2006.01) |
| *H01L 29/20* | (2006.01) |

(52) U.S. Cl.
CPC ............ *A61B 5/0006* (2013.01); *A61B 5/021* (2013.01); *A61B 5/04017* (2013.01); *A61B 5/0452* (2013.01); *A61B 5/0478* (2013.01); *A61B 5/1102* (2013.01); *A61B 7/045* (2013.01); *G01N 27/129* (2013.01); *G01N 33/0004* (2013.01); *H01L 29/205* (2013.01); *A61B 5/002* (2013.01); *A61B 5/08* (2013.01); *A61B 5/6898* (2013.01); *A61B 5/7225* (2013.01); *A61B 2560/0242* (2013.01); *A61B 2562/164* (2013.01); *H01L 29/2003* (2013.01); *H01L 29/7786* (2013.01)

(58) Field of Classification Search
CPC ........... H01L 29/42316; H01L 21/8252; H01L 29/66212; H01L 29/872
USPC .......................................... 600/372, 382–393
See application file for complete search history.

(56) References Cited

U.S. PATENT DOCUMENTS

| | | | |
|---|---|---|---|
| 2008/0006845 A1 | 1/2008 | Derluyn et al. | |
| 2008/0265258 A1* | 10/2008 | Tanabe | H01L 29/7787 257/76 |
| 2009/0072272 A1* | 3/2009 | Suh | H01L 29/7783 257/194 |
| 2011/0199102 A1* | 8/2011 | Garcia | G01N 27/4148 324/658 |
| 2012/0149161 A1* | 6/2012 | Ohki | H01L 29/66462 438/270 |
| 2013/0111977 A1 | 5/2013 | Offermans et al. | |
| 2014/0203797 A1* | 7/2014 | Stivoric | G01K 1/022 324/76.11 |
| 2014/0239309 A1* | 8/2014 | Ramdani | H01L 29/2003 257/76 |
| 2014/0266324 A1* | 9/2014 | Teo | H01L 29/7831 327/109 |
| 2014/0323895 A1 | 10/2014 | Vitushinsky et al. | |
| 2015/0069409 A1* | 3/2015 | Dargis | H01L 21/02505 257/76 |

OTHER PUBLICATIONS

International Search Report PCT/IB2017/051325 Completed Jun. 28, 2017; dated Jul. 7, 2017 5 pages.
Written Opinion of the International Searching Authority PCT/IB2017/051325 dated Jul. 7, 2017 10 pages.

* cited by examiner $V_G \gg V_T$ $V_G = 0$
$V_G > V_T$ $V_G \ll V_T$

Best possible resolution at MA6 hard contact with AZ4533 is 2 μm

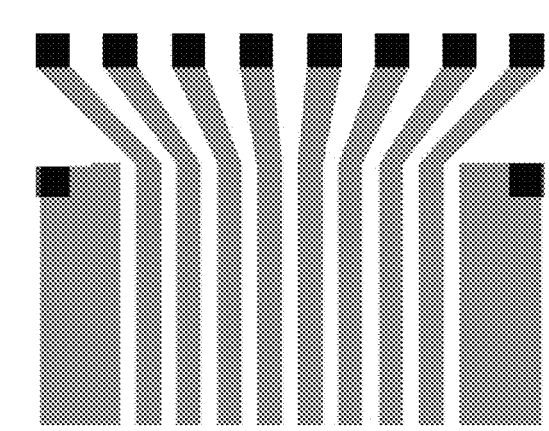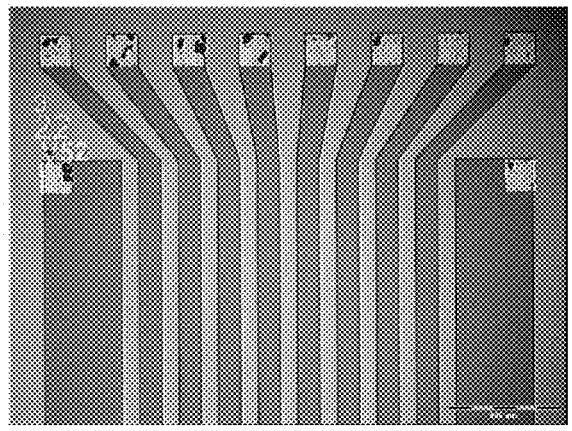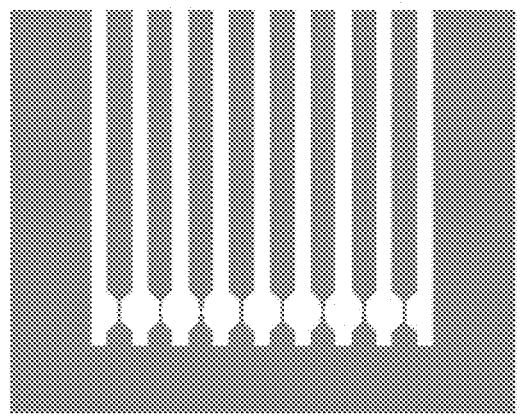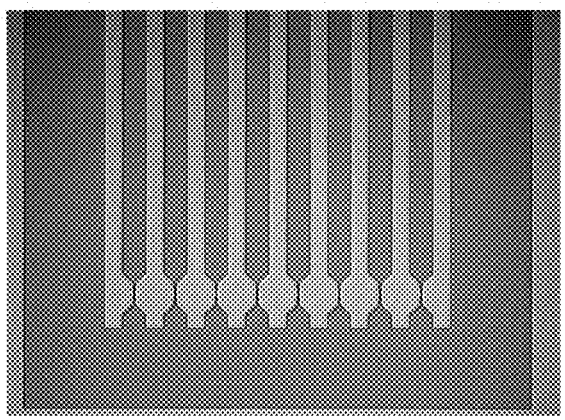
Fig. 5d　　　　　　　　　　Fig. 5e

Alignment precision on 25 x 25 mm² samples is ± 2 μm

200 μm

AZ4533 after development, prepared for ion implantation
2DEG channels (dark) patterned by ion-implantation after the resist removal
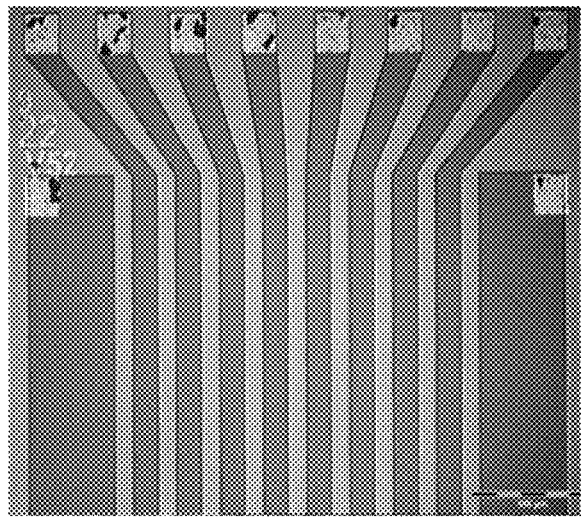
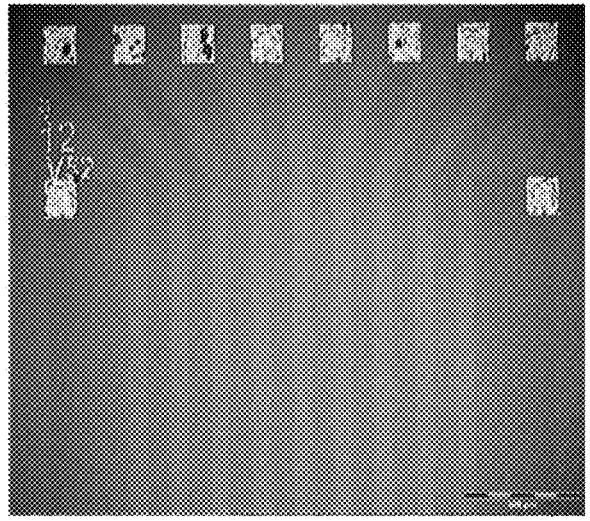
Fig. 5i
Fig. 5j
Fig. 5k
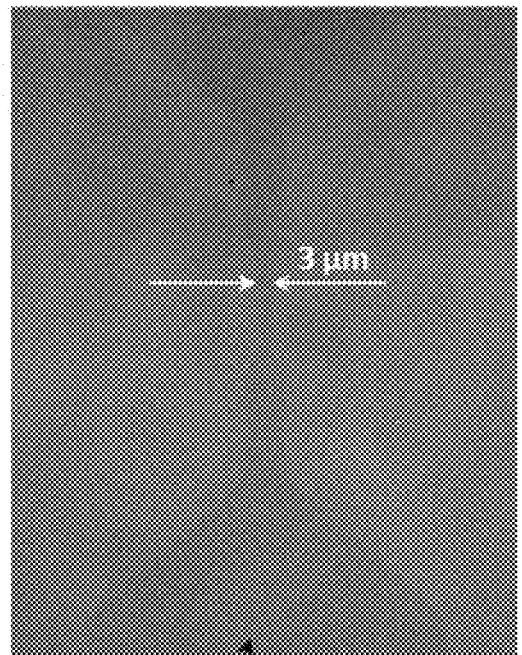
Visible non-implanted area (in dark) containing the conductive 2DEG channel

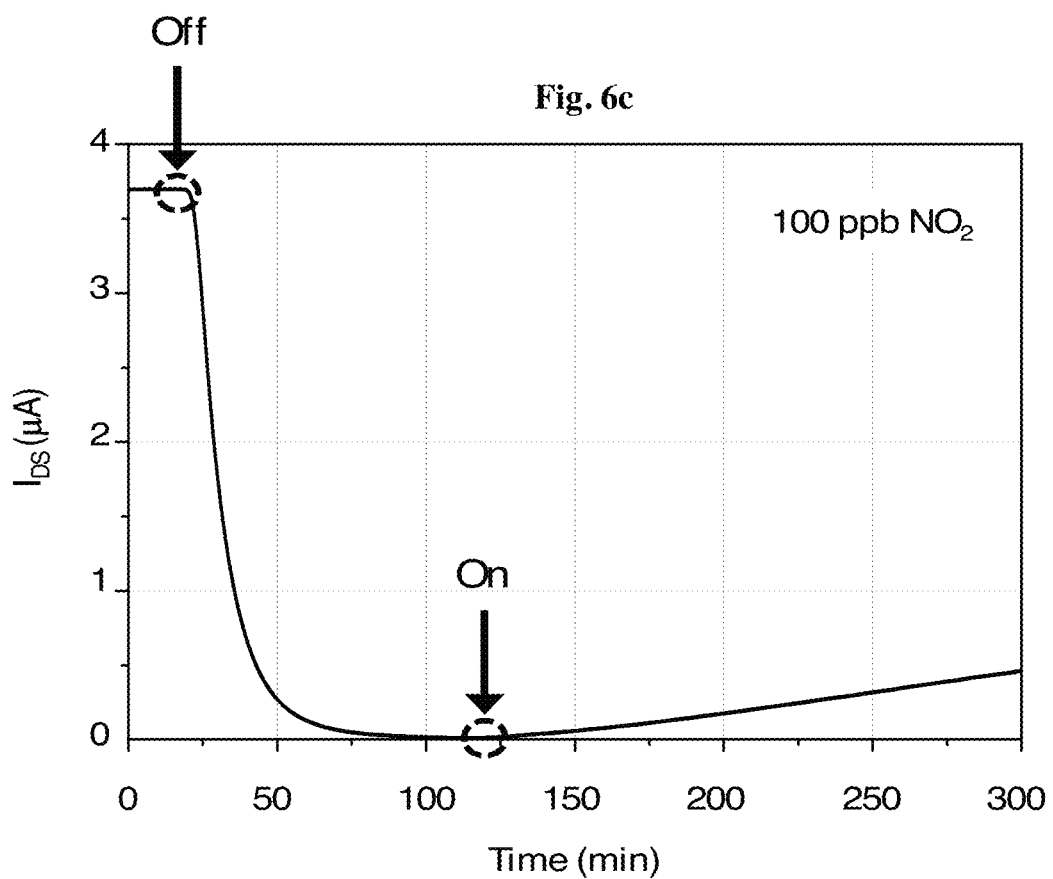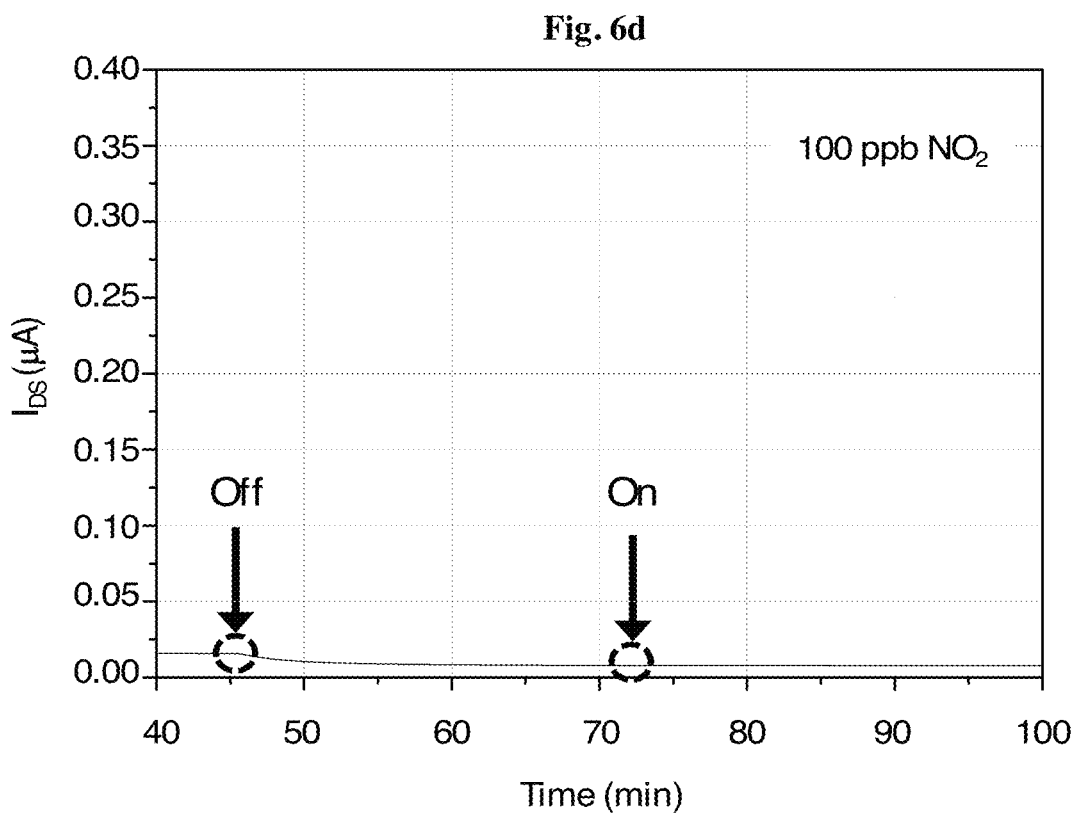

Fig. 7a          Ga-Face Polarity
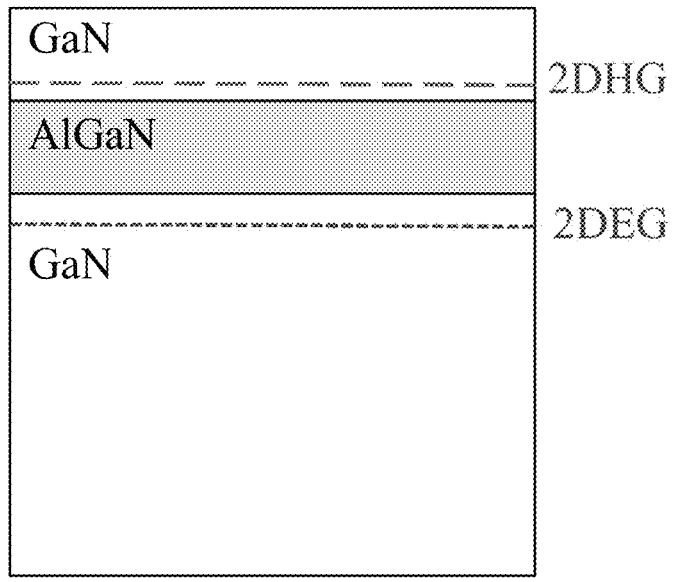
Fig. 7b          N-Face Polarity
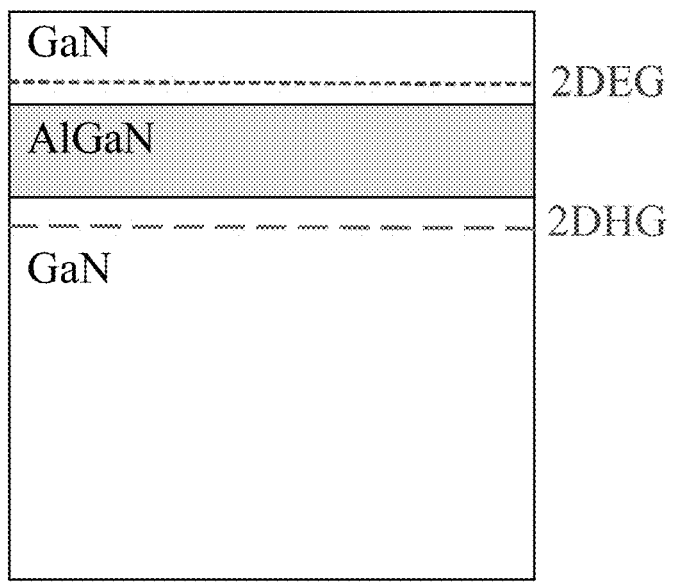

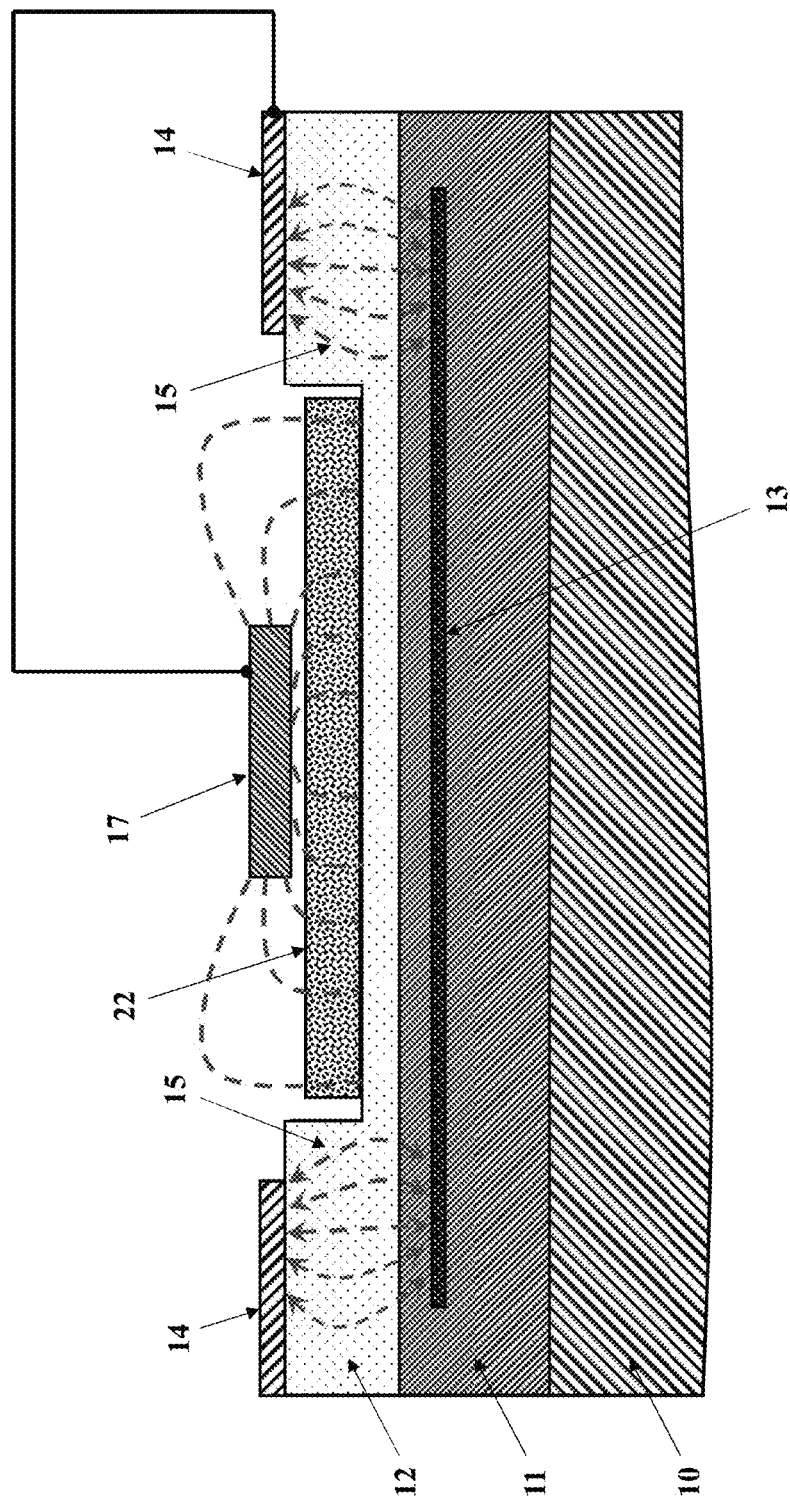

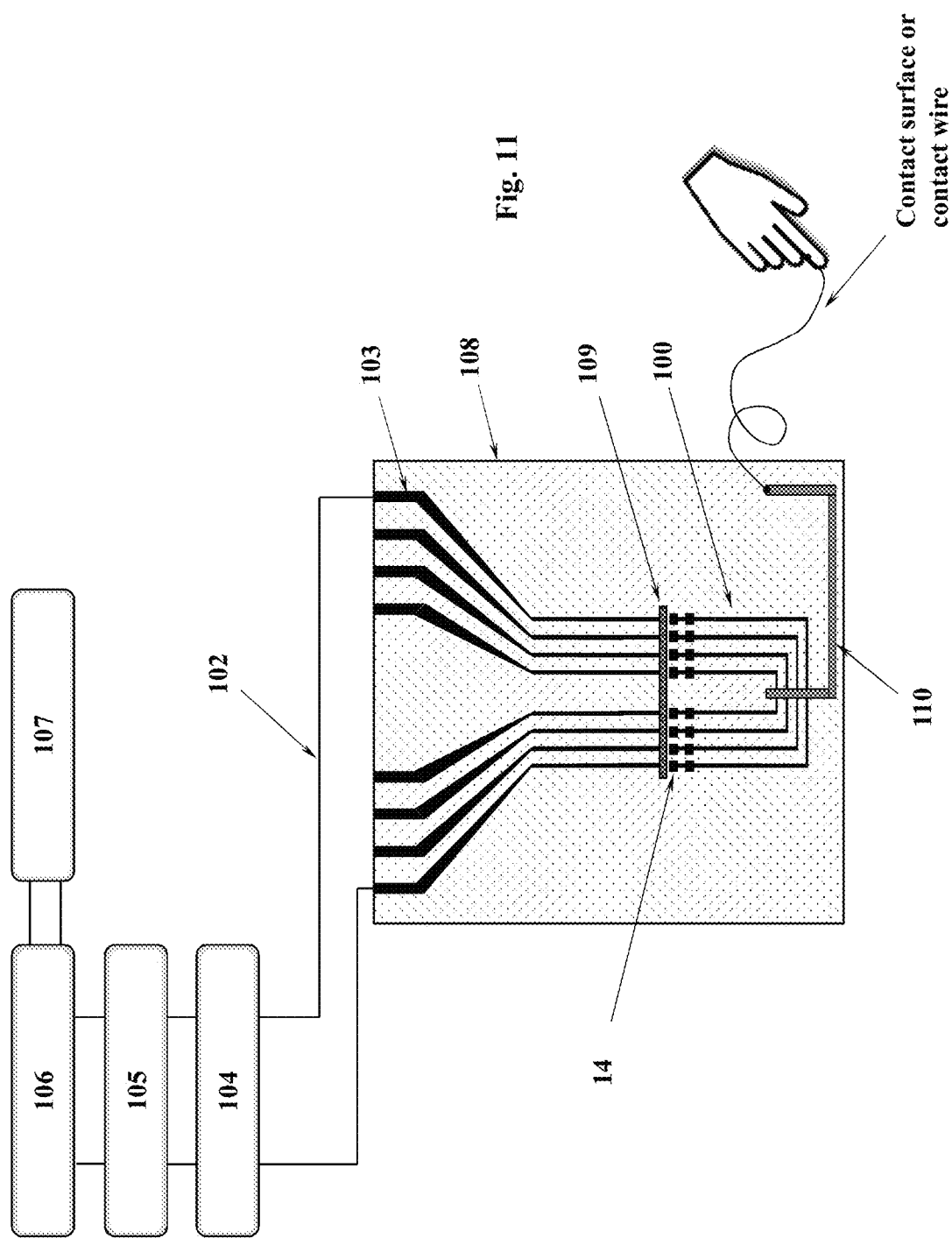

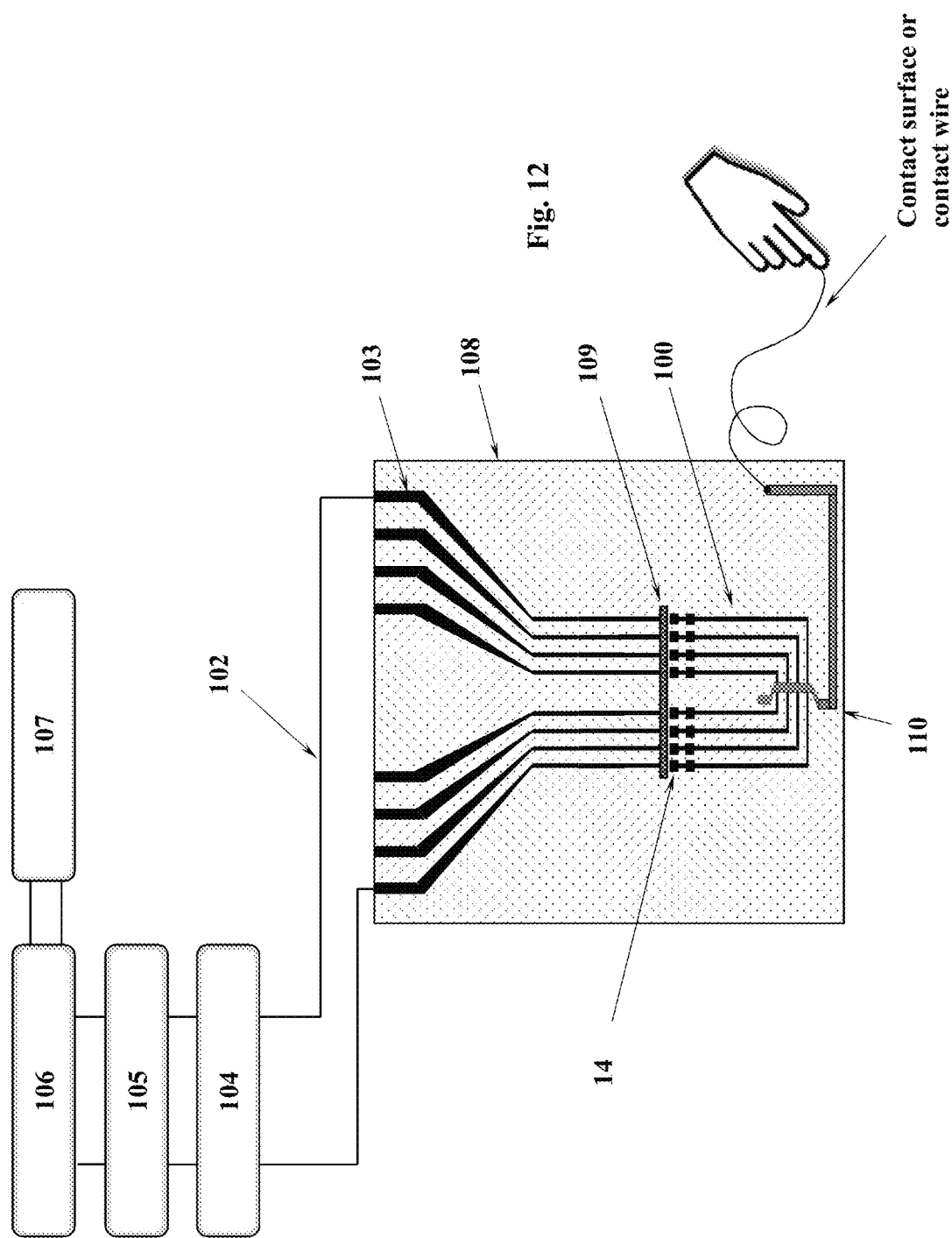

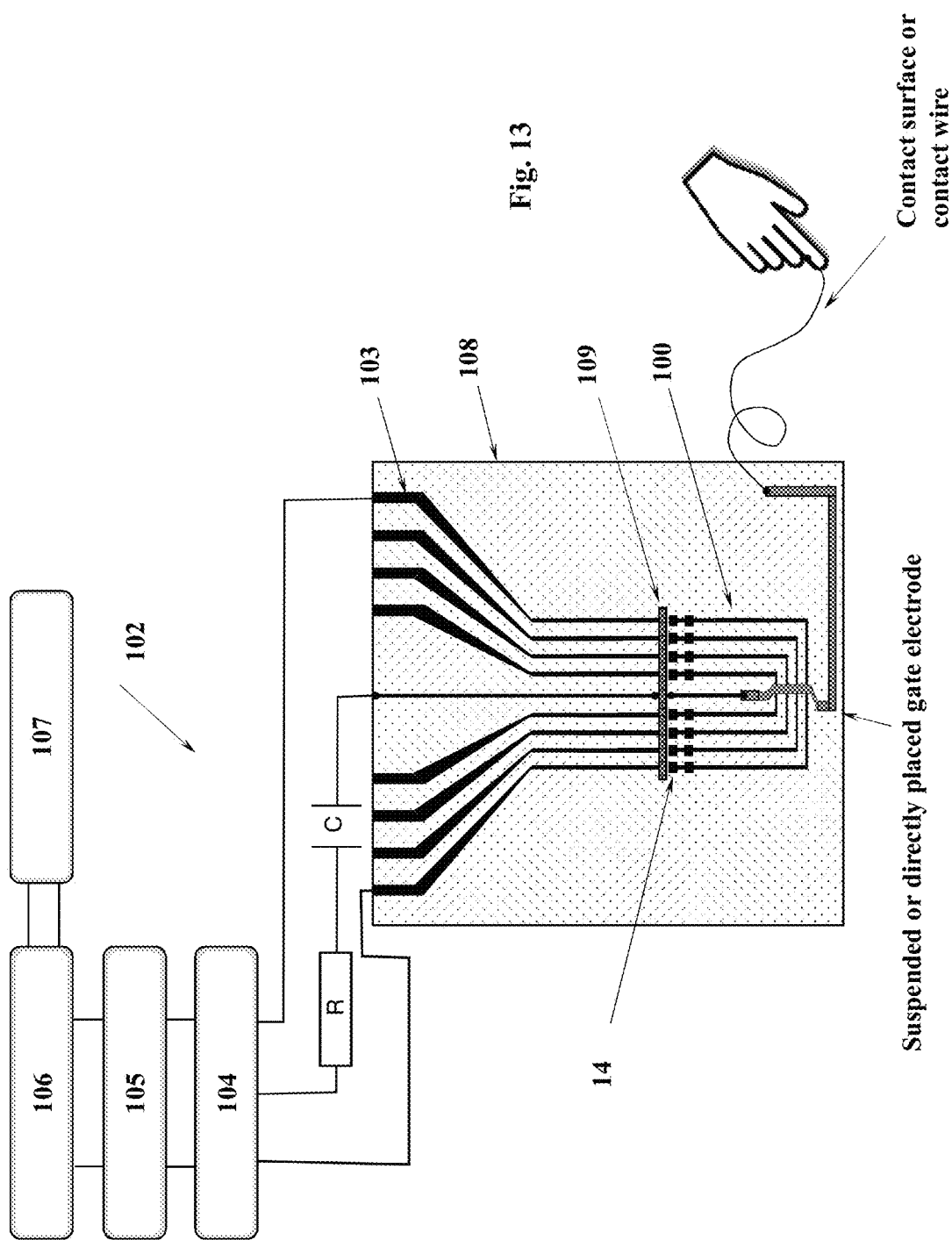

MICROELECTRONIC SENSOR FOR AIR QUALITY MONITORING

RELATED APPLICATIONS

This application is a Continuation-In-Part of PCT Patent Application No. PCT/IB2017/051325 having International filing date of Mar. 7, 2017, which claims the benefit of priority of U.S. patent application Ser. No. 15/067,093 filed on Mar. 7, 2017, of U.S. patent application Ser. No. 15/157,285 filed on May 17, 2016, and U.S. Provisional Application No. 62/362,167 filed on Jul. 14, 2016. The contents of the above applications are all incorporated by reference as if fully set forth herein in their entirety.

TECHNICAL FIELD

The present application relates to the field of microelectronic sensors based on high-electron-mobility transistors. In particular, the present application relates to the open-gate pseudo-conductive high-electron-mobility transistors and their use in an air quality monitoring.

BACKGROUND

Nowadays, one of the basic missions of humankind is to preserve and improve the quality of air. To accomplish this, the air quality must be monitored, and the status of the atmosphere must be evaluated as compared to clean air standards. In the 1970s, the first regulations on air pollutants were implemented in the United States. Since that time, many significant reductions on all types of air pollutants have been made. However, bad air quality, smog and acid rains continue to threaten health and environment of people. Nonetheless, many people are not concerned about air quality simply because they are not easily able to know how clean the air around them really is, but just assume it is clean enough.

Therefore, there is a high demand for ultrasensitive, compact, portable and even wearable, low-cost, continuous air quality monitoring device. In order to provide real-time air quality readings for the immediate surroundings, the air quality monitoring device may either communicate with the user's gadget, such as a smartphone or an electronic watch, or be used as a standalone sensor.

One of the ideas behind the air quality monitoring devices is that they allow everyday people to be more proactive when it comes to air pollution. Users could avoid polluted areas where the levels are dangerously high, for example, and would perhaps be more motivated to pressure local authorities to do something about the problem.

Seemingly, the air quality within our homes can be up to eight times worse than outdoors, and on specific occasions, such as reconstruction or repainting, way more than that too. Indoor air quality can also deteriorate due to activities like cooking, which introduces smoke and other particulate matter. Cleaning and other indoor activities can introduce Volatile Organic Chemicals (VOCs). Home building materials and the furniture may also release the VOCs. In the process of trying to secure our homes by locking doors and keeping the windows shut, we may also inadvertently seal in our expiratory carbon dioxide, while furnaces and other wood-fuelled heaters produce carbon monoxide.

There are four major gas pollutants having effects on human health, which are identified by environmental protection authorities and regulated in many areas of the world: ozone, nitrogen oxides, sulphur dioxide and carbon monoxide. Ozone is normally found in the upper atmosphere forming a protective ozone layer that protects us from harmful UV rays. However, in the lower atmosphere, ozone can reduce lung functions, being especially harmful for people with asthma, lung disease, or other respiratory problems. Ozone is created by chemical reactions between nitrogen oxides ($NO_x$) and volatile organic compounds with the addition of sunlight. It is the primary component of smog and is more prevalent on hot and sunny days.

Nitrogen oxides ($NO_x$) act as precursors to more harmful gases, such as ozone. Nitrogen dioxide ($NO_2$) can form a reddish-brown layer over urban areas. Unlike ozone, it is more prevalent in the winter months and the reddish-brown layer over cities becomes worse in the winter. Acid rains are formed from $NO_2$ and sulphur dioxide ($SO_2$). Along with other chemicals, $NO_x$ can cause the creation of other toxic gases, nutrient loading in water systems and contribution to global warming.

When fuel, such as oil and coal, or other raw materials are burned, sulfur present therein transforms to sulphur gas in the form of $SO_2$, which can aggravate lung functions especially for people with pre-existing conditions. As mentioned above, it also causes acid rains, which makes soils and water more acidic and therefore harms plants, trees, and people, through both respiratory-aggravating acid fogs and by increasing the solubility of heavy metals in natural waters.

Carbon monoxide, being an odourless and colourless gas, is totally undetectable to human senses. It is mainly emitted from automobile exhaust, but industrial processes and biomass burning also contribute to CO emissions. It is poisonous if ingested at high levels and strongly affects both the cardiovascular functioning and the nervous system by reducing the amount of oxygen to the rest of the body.

The existing air quality monitoring devices are either costly, bulky or do not provide sensitivity (below 50 ppb) required for continuous air quality monitoring. This is the case of the CitiSense™ sensor recently developed by scientists at the University of California, San Diego. Their device is able to measure local concentrations of ozone, nitrogen dioxide and carbon monoxide, the pollutants emitted most by internal combustion vehicles. That data is wirelessly transmitted to the user's smartphone, where it is displayed on the screen via a custom application along with an actual number rating.

The most sensitive devices for gas monitoring developed recently are based on carbon nanotubes (CNT), two dimensional electron gas (2DEG) or graphene. The graphene and CNT technologies are still rather complicated showing lack of long term stability. In contrast, 2DEG-based devices offer the same sensitivity combined with much higher life time, improved resolution, response time and minimal power consumption.

High Electron Mobility Transistor

The polarization doped high-electron-mobility transistor (HEMT) is a field effect transistor (FET) in which two layers of different bandgap and polarisation field are grown upon each other forming a hetero-junction structure. As a consequence of the discontinuity in the polarisation field, surface charges are created at the interface between the layers of the hetero-junction structure. If the induced surface charge is positive, electrons will tend to compensate the induced charge resulting in the formation of the channel. Since in the HEMT, the channel electrons are confined in a quantum well in an infinitely narrow spatial region at the interface between the layers, these electrons are referred to as a two-dimensional electron gas (2DEG). This special confinement of the channel electrons in the quantum well actually grants them two-dimensional features, which strongly enhance their mobility surpassing the bulk mobility of the material in which the electrons are flowing.

The HEMTs based on the layers of III-V semiconductor materials, such as gallium nitride (GaN) and aluminium gallium nitride (AlGaN), have recently been developed with a view to high-voltage and high-power switching applications. The high voltages and high switching speeds allow smaller, more efficient devices, such as home appliances, communications and automobiles to be manufactured. To control the density of electrons in the 2DEG channel and to switch the HEMT on and off, the voltage at the gate of the transistor should be regulated.

FIGS. 1a-1c schematically shows the quantum well at three different biasing conditions starting from the positive gate potential ($V_G$), much higher than the threshold voltage ($V_T$), and going down to the 0V gate potential and further to the negative values below the threshold voltage. The $V_T$ is defined as a voltage required populating electrons at the interface between the GaN and AlGaN layers, thereby creating conductivity of the 2DEG channel. Since the 2DEG channel electrons occupy energy levels below the Fermi level, the Fermi level in a quantum well is located above several energy levels when $V_G \gg V_T$ (FIG. 1a). This enables high population of the 2DEG channel electrons and hence, high conductivity. The HEMT is turned on in this case. However, when $V_G$ decreases to 0V (FIG. 1b), the Fermi level also drops with respect to the quantum well. As a result, much fewer electron energy levels are populated and the amount of the 2DEG channel electrons significantly decreases. When $V_G \ll V_T$ (FIG. 1c), all electron energy levels are above the Fermi level, and there is no 2DEG electrons below the gate. This situation is called "channel depletion", and the HEMT is turned off.

Many commercially available AlGaN/GaN-based HEMT structures have a negative $V_T$, resulting in a "normally-on" operation mode at 0V gate potential. They are called "depletion-mode transistors" and used in various power switching applications when the negative voltage must be applied on the gate in order to block the current. However, for safe operation at high voltage or high power density, in order to reduce the circuit complexity and eliminate standby power consumption, HEMTs with "normally-off" characteristics are preferred.

Several techniques to manufacture the normally-off HEMTs have been reported. Burnham et al (2010) proposed normally-off structures of the recessed gate type. In this structure, the AlGaN barrier layer is etched and the gate is brought closer to the interface between the AlGaN barrier layer and the GaN buffer layer. As the gate approaches the interface between the layers, the $V_T$ increases. The normally-off operation of the transistor is achieved once the depletion region reaches the interface and depletes the 2DEG channel at zero gate voltage. The major advantages of these HEMTs are relatively lower power consumption, lower noise and simpler drive circuits. These HEMTs are currently used, for example, in microwave and millimetre wave communications, imaging and radars.

Chang et al (2009) proposed instead of etching the relatively thick barrier layer to approach the AlGaN/GaN interface, to use a very thin AlGaN barrier. This structure also achieves normally-off operation by approaching the gate towards the AlGaN/GaN interface. Chen et al (2010) proposed to use the fluorine-based plasma treatment method. Although many publications have adopted various methods to achieve normally-off devices with minimum impact on the drain current, they unfortunately sacrificed device turn-on performance.

SUMMARY

The present application describes embodiments of a microelectronic sensor, which is based on a pseudo-conductive high-electron mobility transistor (PC-HEMT). In some embodiments, a transistor comprises a substrate, on which a multilayer hetero-junction structure is deposited. This hetero-junction structure may comprise at least two layers, a buffer layer and a barrier layer, which are grown from III-V single-crystalline or polycrystalline semiconductor materials. In another configuration, the hetero-junction structure is placed on free-standing membranes, which are actually free-standing columns of substrate composed of sapphire, silicon, silicon carbide, gallium nitride or aluminium nitride, having thickness of 0.5-2 μm, for creating mass-loading effect and allowing a pressure sensing mode of the sensor.

A conducting channel comprising a two-dimensional electron gas (2DEG), in case of two-layers configuration, or a two-dimensional hole gas (2DHG), in case of three-layers configuration, is formed at the interface between the buffer and barrier layers and provides electron or hole current in the system between source and drain electrodes. The source and drain contacts are capacitively-coupled (non-ohmic) contacts connected to the formed 2DEG/2DHG channel and to electrical metallizations, the latter are placed on top of the transistor and connect it to the sensor system. An optional dielectric layer is deposited on top of the hetero-junction structure. The open gate area of the transistor is formed between the source and drain areas as a result of recessing or growing of the top layer to a specific thickness.

If the source and drain contacts are non-ohmic (capacitively-coupled), in order to electrically contact the 2DEG/2DHG channel underneath, which is about 5-20 nm bellow metallizations, the AC-frequency regime is used. The capacitive coupling of the non-ohmic metal contacts with the 2DEG/2DHG channel is normally induced at the frequency higher than 30 kHz. In the case of non-ohmic contacts, the DC readout cannot be carried out. Instead, the AC readout or impedance measurements of the electric current flowing through the 2DEG/2DHG-channel are performed.

In some embodiments, the significant features of the PC-HEMT structure are that:
(i) the thickness of the top layer in the open gate area between the source and drain contacts is 5-9 nm, preferably 6-7 nm, more preferably 6.3 nm, and that corresponds to the pseudo-conducting current range between normally-on and normally-off operation mode of the transistor,
(ii) the surface of the top layer within the open gate area between the source and drain contacts has a roughness of about 0.2 nm or less, preferably 0.1 nm or less, more preferably 0.05 nm, and
(iii) the non-ohmic source and drain contacts for the capacitive coupling with the conductive 2DEG/2DHG channel optionally replace the ohmic contacts.

In some embodiments, the PC-HEMT multilayer hetero-junction structure of the present application is grown from any available III-V single-crystalline or polycrystalline semiconductor materials, such as GaN/AlGaN, GaN/AlN, GaN/InN, GaN/InAlGaN, GaAs/AlGaAs GaN/InAlN, InN/InAlN, and LaAlO$_3$/SrTiO$_3$. In case of the GaN/AlGaN PC-HEMT, it has been surprisingly found that in the open gate area of the PC-HEMT, the thickness of the top layer that corresponds to the pseudo-conducting current range between normally-on and normally-off operation mode of the PC-HEMT, is about 6-7 nm.

In a particular embodiment, the hetero-junction structure may be a three-layer structure consisting of two buffer layers and one barrier layer squeezed between said buffer layers like in a sandwich. This may lead to formation of the two-dimensional hole gas (2DHG) in the top buffer layer above the barrier layer which results in reversing polarity of the transistor.

In some embodiments, the present application provides the PC-HEMT-based microelectronic sensor for ultrasensitive, continuous air quality monitoring.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Disclosed embodiments will be understood and appreciated more fully from the following detailed description taken in conjunction with the appended figures. The drawings included and described herein are schematic and are not limiting the scope of the disclosure. It is also noted that in the drawings, the size of some elements may be exaggerated and, therefore, not drawn to scale for illustrative purposes. The dimensions and the relative dimensions do not necessarily correspond to actual reductions to practice of the disclosure.

FIGS. 5d-5e show the mask and the corresponding lithographic image, respectively, of the sensor layout of the present invention.

FIG. 5i shows the lithographic image of the sensor layout with the AZ4533 resist after development, prepared for ion implantation.

FIG. 5j shows the 2DEG channels (dark) patterned by ion-implantation after the resist removal.

FIG. 5k shows the visible non-implanted area containing the conductive 2DEG channel.

FIG. 6c shows the time-dependent plot of the drain-source electric current $I_{DS}$ of the nitrogen oxide sensor measuring 100 ppb of the $NO_2$ gas in humid air, where the sensor is based on the PC-HEMT made by the manufacturing process of the present invention.

FIG. 6d shows the time-dependent plot of the drain-source electric current $I_{DS}$ of the nitrogen oxide sensor measuring 100 ppb of the $NO_2$ gas in humid air, where the sensor is based on the HEMT made by a conventional manufacturing process.

FIG. 7a schematically shows the formation of the 2DEG and 2DHG conducting channels in the Ga-face three-layer GaN/AlGaN/GaN PC-HEMT structure.

FIG. 7b schematically shows the formation of the 2DEG and 2DHG conducting channels in the N-face three-layer GaN/AlGaN/GaN PC-HEMT structure.

FIG. 10 schematically shows a cross-sectional view of the PC-HEMT configuration of embodiments with a mechanically suspended metal gate and a porous material filling an open gate area.

FIG. 11 schematically shows a PC-HEMT-based microelectronic sensor of embodiments with a common suspended metal gate electrode.

FIG. 12 schematically shows a PC-HEMT-based microelectronic sensor of embodiments with a common mechanically suspended metal gate electrode, which has no physical contact with the PC-HEMT or array thereof.

FIG. 13 schematically shows a PC-HEMT-based microelectronic sensor of embodiments with a common metal gate electrode placed in contact with the PC-HEMT or array thereof and discharged via the connection to a source electrode.

DETAILED DESCRIPTION

Figure 1A:
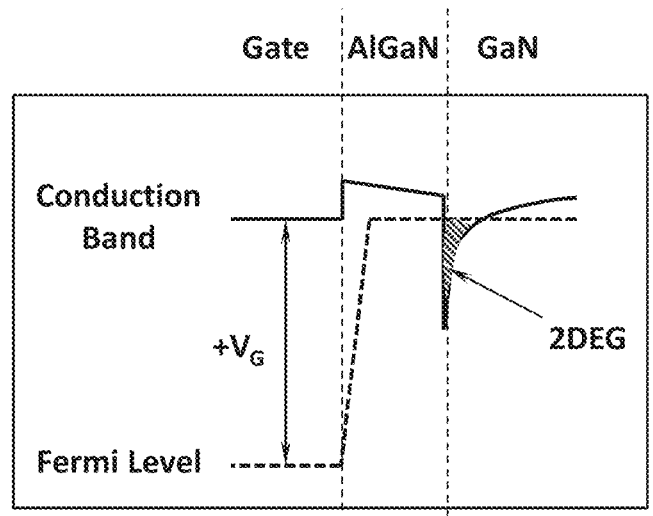
FIG. 1(a) the positive gate potential ($+V_G$), much higher than the threshold voltage ($V_T$), FIG. 1(b) 0V gate potential, and FIG. 1(c) negative gate potential ($-V_G$) below the threshold voltage ($V_T$).
Figure 1B:
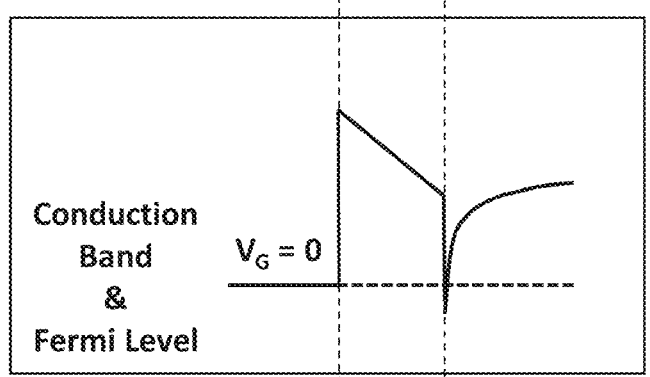
FIG. 1 schematically shows the quantum well at three different biasing conditions.
Figure 1C:
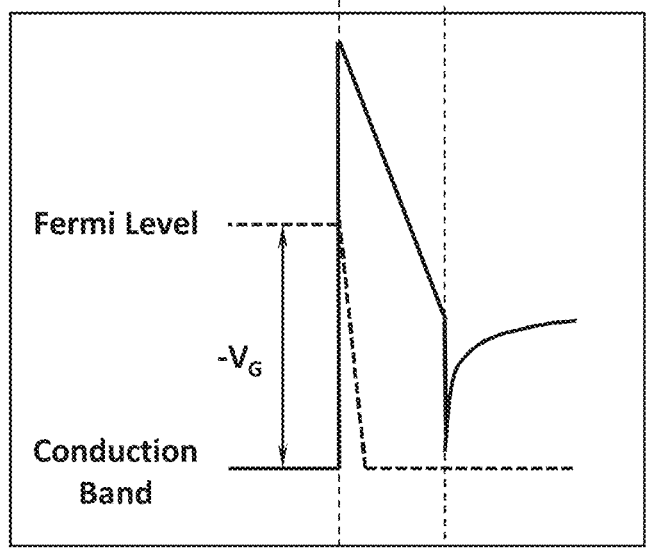

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising x and z" should not be limited to devices consisting only of components x and z. As used herein, the term "about" means there is a 10% tolerance of the mentioned or claimed value. As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The air quality monitoring sensor of an embodiment is based on the open-gate pseudo-conductive high-electron mobility transistor (PC-HEMT) disclosed in the co-pending patent application U.S. Ser. No. 15/067,093 and U.S. Ser. No. 15/157,285. The phenomenon of the pseudo-conductive current described in those applications makes the PC-HEMT-based sensor of an embodiment extremely sensitive.

The present application describes embodiments of a microelectronic sensor for air quality monitoring comprising:
1) an array of open-gate pseudo-conductive high-electron mobility transistors printed on a flexible printed circuit board (PCB), and connected to their dedicated electrical contact lines printed on said PCB;
2) one common metal gate electrode electrically connected to a contact surface or to a contact wire and placed over said transistors at the height of 10-100 nm, without physical contact with said transistors;
3) a voltage source connected to said electrical contact lines via an electric circuit for supplying electric current to said transistors;
4) an integrated or CMOS current amplifier connected to said voltage source for amplification of an electric current obtained from said transistors;
5) an analogue-to-digital converter (ADC) with in-built digital input/output card connected to said current amplifier for outputting the converted signal to an external memory; and
6) a connection module for connecting the sensor to the external memory;
characterised in that each one of said transistors comprises:
(a) a multilayer hetero-junction structure made of gallium nitride (GaN) and aluminium gallium nitride (AlGaN) single-crystalline or polycrystalline semiconductor materials, and deposited on a substrate layer or placed on free-standing membranes;
said structure comprises (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have Ga-face polarity, thus forming a two-dimensional hole gas (2DHG) conducting channel in the top GaN layer, close to the interface with said AlGaN barrier layer; or
said structure comprises (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have N-face polarity, thus forming a two-dimensional electron gas (2DEG) conducting channel in the top GaN layer, close to the interface with said AlGaN barrier layer; or
said structure comprises (i) one top AlGaN layer recessed in an open gate area of the transistor to the thickness of 5-9 nm and having the surface roughness of 0.2 nm or less, and (ii) one bottom GaN buffer layer; said layers have N-face polarity, thus forming a two-dimensional hole gas (2DHG) conducting channel in the GaN buffer layer, close to the interface with said AlGaN barrier layer; and
(b) source and drain contacts connected to said 2DEG or 2DHG conducting channel and to electrical metallizations for connecting said transistor to an electric circuit.

Figure 2A:
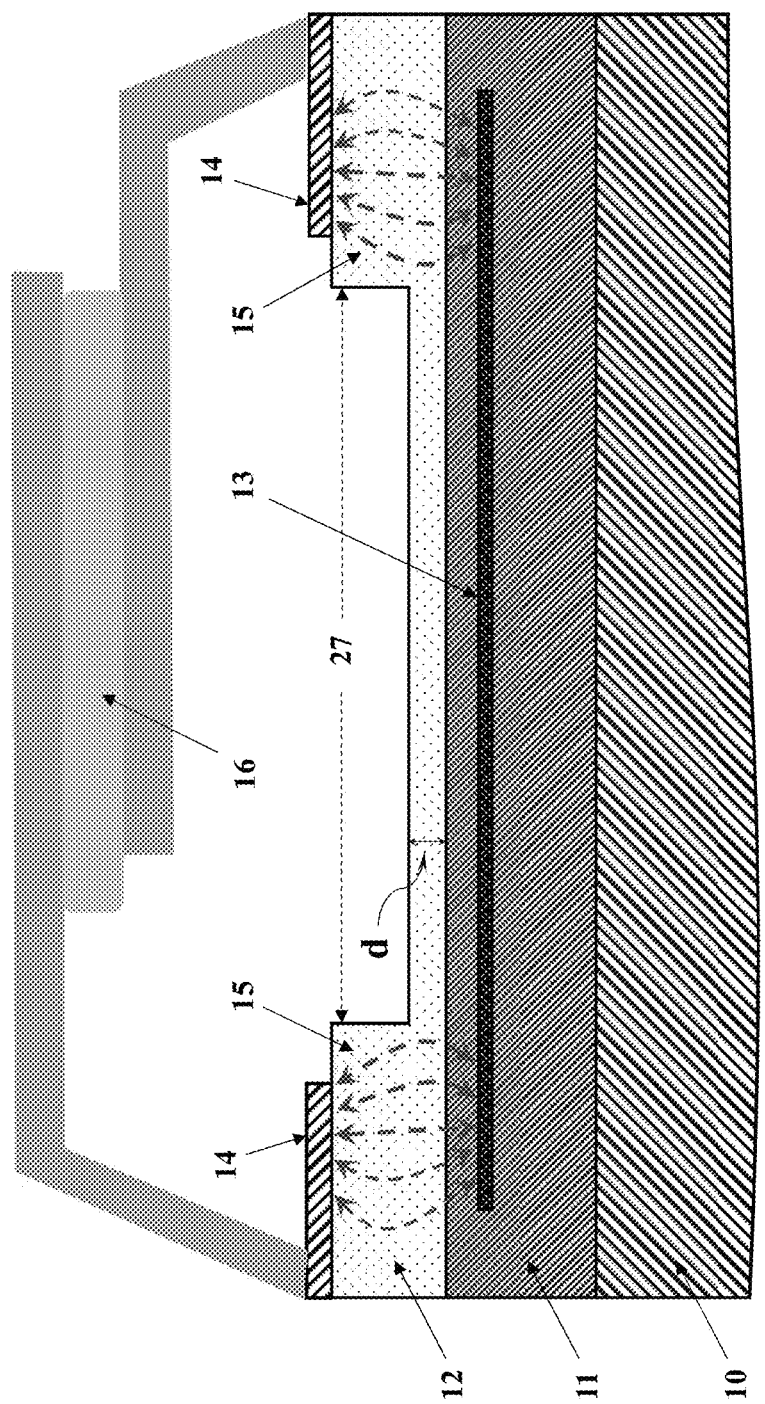
FIG. 2a shows a cross-sectional view of an open-gate pseudo-conductive high-electron mobility transistor (PC-HEMT) with a gas permeable membrane and without a dielectric layer of an embodiment of the present application.

In one aspect of the disclosure, FIG. 2a shows a cross-sectional view of an open-gate pseudo-conductive high-electron mobility transistor (PC-HEMT) of an embodiment of the present application comprising:

a multilayer hetero-junction structure made of III-V single-crystalline or polycrystalline semiconductor materials, said structure comprising at least one buffer layer (11) and at least one barrier layer (12), said layers being stacked alternately, and said structure being deposited on a substrate layer (10);

a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain non-ohmic contacts;

electrical metallizations (14) capacitively-coupled to said 2DEG or 2DHG channel (13) for inducing displacement currents (15), thereby creating non-ohmic source and drain contacts connecting said transistor to an electric circuit;

a gas permeable membrane (16) allowing a minimum gas flow necessary for creating an open gate; and an open gate area (27) between said source and drain non-ohmic contacts;

wherein:
(i) the thickness of the barrier layer (12) in the open gate area (27) is 5-9 nm which corresponds to the pseudo-conducting current range between normally-on and normally-off operation mode of the transistor, and
(ii) the surface of the barrier layer (12) has a roughness of about 0.2 nm or less.

Figure 2B:
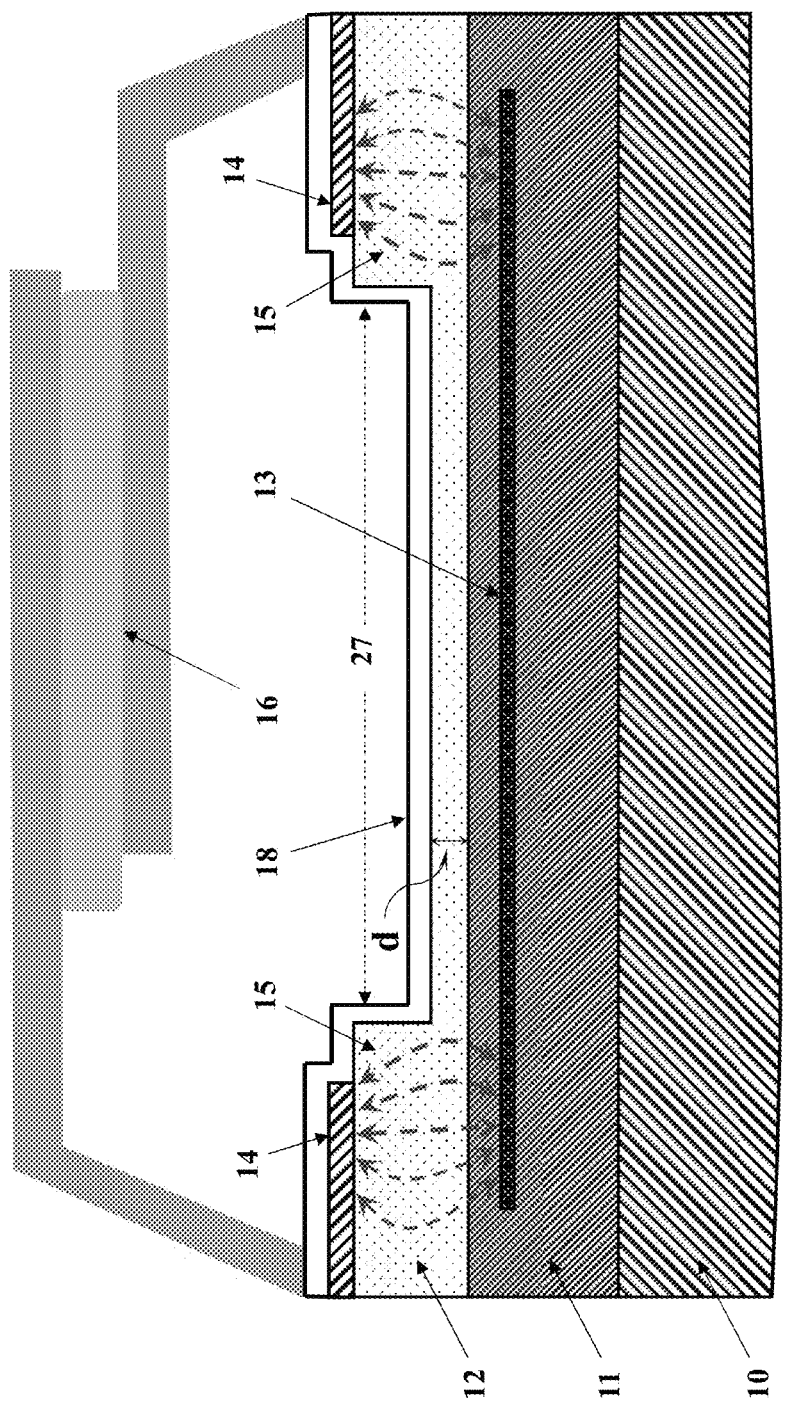
FIG. 2b schematically shows a cross-sectional view of an open-gate pseudo-conductive high-electron mobility transistor (PC-HEMT) with a gas permeable membrane and with a dielectric layer of an embodiment of the present application.

The PC-HEMT, which is shown on FIG. 2a, may further comprise a dielectric layer (18) of approximately 1-10 nm thickness, which is used for device passivation. This dielectric layer (18) is deposited on top of the barrier layer (12), as schematically shown in FIG. 2b. In one embodiment, the dielectric layer (18) is made, for example, of SiO—SiN—SiO ("ONO") stack of 100-100-100 nm thickness or SiN—SiO—SiN ("NON") stack having the same thicknesses. This dielectric layer (18) is deposited on top of the barrier layer by a method of plasma-enhanced chemical vapour deposition (PECVD), which is a stress-free deposition technique.

The 2DEG channel (13) formed near the interface between the buffer layer (11) and the barrier layer (12) serves as a main sensitive element of the transistor reacting to a surface charge and potential. The 2DEG channel (13) is configured to interact with very small variations in surface or proximal charge or changes of electrical field on the barrier layer/liquid-air or barrier layer/metal/liquid-air interfaces interacting with the donor-like surface trap states of the barrier layer. This will be defined and discussed below in detail.

The term "2DEG" mentioned in the following description and claims should not be understood or interpreted as being restricted to the two-dimensional electron gas. As stated above and will be explained later in this application, the two-dimensional hole gas may also be a possible current carrier in a specific hetero-junction structure. Therefore, the term "2DEG" may be equally replaced with the term "2DHG" without reference to any specific PC-HEMT configuration.

"Capacitive coupling" is defined as an energy transfer within the same electric circuit or between different electric circuits by means of displacement currents induced by existing electric fields between circuit/s nodes. In general, ohmic contacts are the contacts that follow Ohm's law, meaning that the current flowing through them is directly proportional to the voltage. Non-ohmic contacts however do not follow the same linear relationship of the Ohm's law. In other words, electric current passing through non-ohmic contacts is not linearly proportional to voltage. Instead, it gives a steep curve with an increasing gradient, since the resistance in that case increases as the electric current increases, resulting in increase of the voltage across non-ohmic contacts. This is because electrons carry more energy, and when they collide with atoms in the conductive channel, they transfer more energy creating new high-energy vibrational states, thereby increasing resistance and temperature.

When electrical metallizations are placed over single-crystalline or polycrystalline semiconductor material, the "Schottky contact" or "Schottky barrier contact" between the metal and the semiconductor occurs. Energy of this contact is covered by the Schottky-Mott rule, which predicts the energy barrier between a metal and a semiconductor to be proportional to the difference of the metal-vacuum work function and the semiconductor-vacuum electron affinity. However, this is an ideal theoretical behaviour, while in reality most interfaces between a metal and a semiconductor follow this rule only to some degree. The boundary of a semiconductor crystal abrupt by a metal creates new electron states within its band gap. These new electron states induced by a metal and their occupation push the centre of the band gap to the Fermi level. This phenomenon of shifting the centre of the band gap to the Fermi level as a result of a metal-semiconductor contact is defined as "Fermi level pinning", which differs from one semiconductor to another. If the Fermi level is energetically far from the band edge, the Schottky contact would preferably be formed. However, if the Fermi level is close to the band edge, an ohmic contact would preferably be formed. The Schottky barrier contact is a rectifying non-ohmic contact, which in reality is almost independent of the semiconductor or metal work functions.

Thus, a non-ohmic contact allows electric current to flow only in one direction with a non-linear current-voltage curve that looks like that of a diode. On the contrary, an ohmic contact allows electric current to flow in both directions roughly equally within normal device operation range, with an almost linear current-voltage relationship that comes close to that of a resistor (hence, "ohmic").

To sum up, FIGS. 2a-2b illustrate the situation when an electrical connection of the transistor to the 2DEG channel is realised via the capacitive coupling to electrical metallizations through a Schottky barrier contact. This coupling becomes possible only if sufficiently high AC frequency, higher than 30 kHz, is applied to the metallizations. The electrical metallizations capacitively coupled to the 2DEG channel utilise the known phenomenon of energy transfer by displacement currents, which are induced by existing electrical fields between the electrical metallizations and the 2DEG conducting channel operated in the AC frequency mode through the Schottky contact, as explained above.

Figure 3:
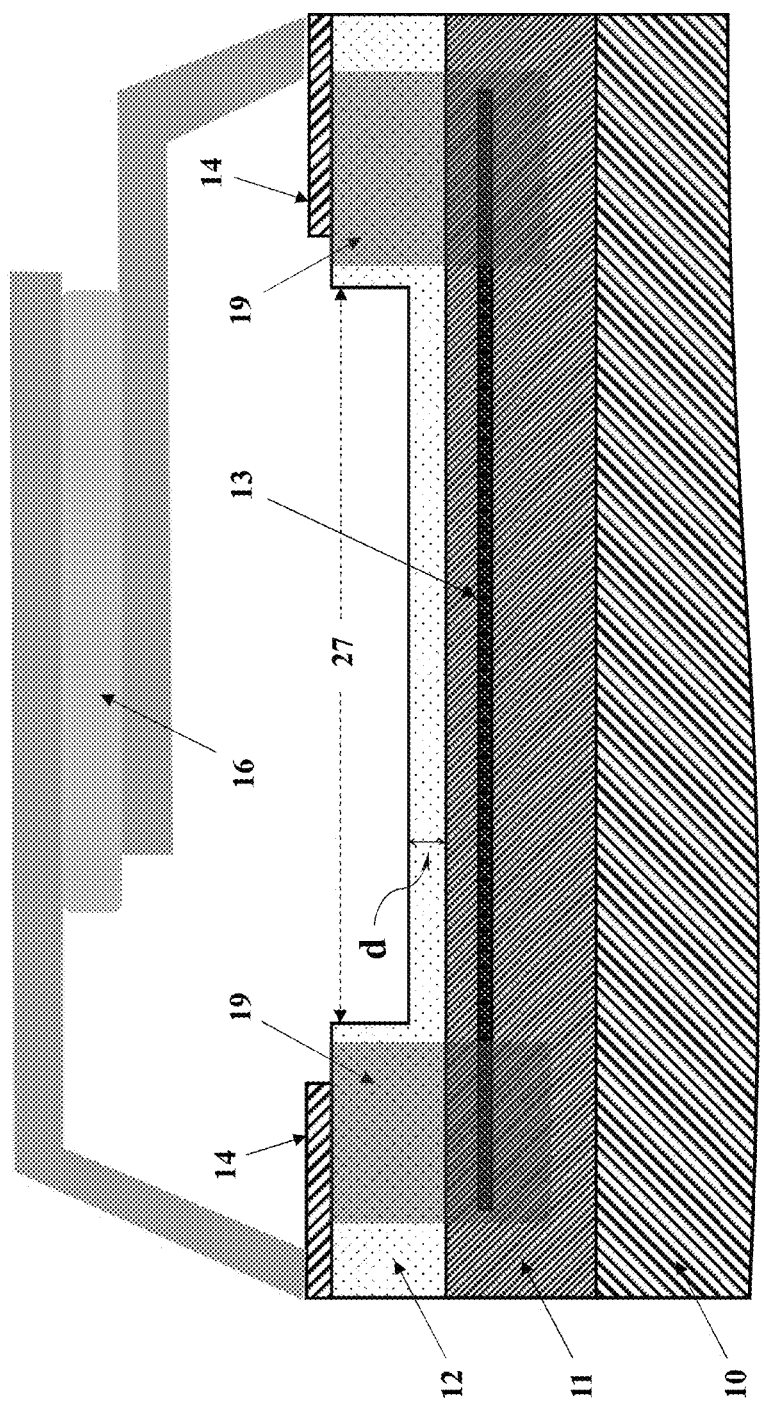
FIG. 3 schematically shows a cross-sectional view of the PC-HEMT of an embodiment of the present application with highly-doped source and drain areas.

Reference is now made to FIG. 3 schematically showing a cross-sectional view of the PC-HEMT of an embodiment of the present application with highly-doped source and drain areas (19). In that case, the strong doping of the source and drain areas may result in a band-edge mismatch. However, if the semiconductor is doped strongly enough, it will form a potential barrier that would be low enough for conducting electrons or holes to have a high probability of tunnelling through, thereby conducting an electric current through the 2DEG channel.

An electrical connection to the 2DEG channel shown in FIG. 3 is realised with highly doped semiconductor areas (19) overlapping the 2DEG channel and having a very low electrical resistance. Dopant ions such as boron ($B^+$), phosphorus ($P^+$) or arsenic ($As^+$) are generally created from a gas source, so that the purity of the source can be very high.

When implanted in a semiconductor, each dopant atom creates a charge carrier in the semiconductor material after annealing. Holes are created for a p-type dopant, and electrons are created for an n-type dopant, modifying conductivity of the semiconductor in its vicinity. $As^+$ can be used for n-type doping, while $B^+$ and $P^+$ ions can be used for p-type doping. For example, in case of the AlGaN/GaN structure, the source and drain areas of the silicon structure are heavily doped with either $B^+$ or $P^+$ to create an electrical connection to the 2DEG or 2DHG channel. The silicon layers have a very low electrical junction resistance between each other in that case, and in order to induce an electrical current in the 2DEG channel, the metallizations are placed on top of the source and drain areas and connected to a circuit.

The third option would be the use of the photoeffect that may also induce an electric current in the 2DEG channel. In order to couple the light excitation with the electronic effects in the conductive 2DEG channel, a photoeffect in a silicon layer should be created. Regarding the direct photoeffect, it is well known that light can only be absorbed when the energy of the absorbed photon ($E=h\nu$) is large enough for an electron to be excited into the valence band. In that case, $E$ is the photon energy, $h$ is Planck's constant and $\nu$ is the frequency of the photon. The frequency is coupled to the wavelength $\lambda$ of light by the constant speed of light $c=\lambda\nu$. Typically the bandgap of silicon at room temperature is 1.12 eV, which means that silicon becomes transparent for wavelength larger than 1240 nm, which is the near infrared range.

For smaller wavelength (i.e. larger energy of the photons), electron/hole pairs are generated leading to a photocurrent. In the fully-depleted, intrinsically doped silicon structures, this results in a higher charge carrier density and consequently, higher sensitivity. For these structures, light is adsorbed in the whole visible range making such devices ideal photodetectors. The mechanism that allows the silicon semiconductor to become photosensitive to irradiation with light has already been described in literature. In the direct photoeffect, it can be tuned by the size, crystalline direction and surface termination. These effects originate from two-dimensional quantum confinement of electrons in the nano-sized 2DEG structure.

Although irradiation of the silicon structure with light of larger wavelengths with photon energies below the bandgap does not have enough energy to excite carriers from the valence to the conduction band in bulk silicon, the electron/hole pairs can also be generated between the valence band and surface states, and the donor-like surface trap states can still be formed (see the definition and explanation of the surface trap states below). The electrons actually deplete the holes trapped at the surface and hence, modulate the gate field. The photogenerated holes are confined to the centre of the silicon structure by the gate field, where they increase the conduction of the 2DEG channel, because of the band bending. The holes increase the channel conductivity for a certain lifetime until they are trapped (recaptured) at the surface. The gain of the transistor can be extremely huge if this re-trapping lifetime is much longer than the holes transit time.

Since the source and drain contacts are non-ohmic (capacitively-coupled), in order to electrically contact the 2DEG channel underneath, which is about 5-20 nm bellow metallizations, the AC frequency regime is used. The capacitive coupling of the non-ohmic metal contacts with the 2DEG channel is normally induced at the frequency higher than 30 kHz. In the case of non-ohmic contacts, the DC readout cannot be performed. Instead, the AC readout or impedance measurements of the electric current flowing through the 2DEG channel are carried out.

In some embodiments, the significant features of the PC-HEMT structure are that:
(i) the non-ohmic source and drain contacts for the capacitive coupling with the conductive 2DEG channel are used,
(ii) the thickness of the barrier layer in the open gate area is 5-9 nm which corresponds to the pseudo-conducting current range between normally-on and normally-off operation mode of the transistor, and
(iii) the surface of the barrier layer has a roughness of about 0.2 nm or less.

In a specific embodiment, the III-V semiconductor materials are selected from the pairs GaN/AlGaN, GaN/AlN, GaN/InN, GaN/InAlN, InN/InAlN, GaN/InAlGaN, GaAs/AlGaAs and $LaAlO_3/SrTiO_3$.

In another embodiment, electrical metallizations (14) connect the transistor to an electric circuit and allow electric current to flow between the non-ohmic contacts, which are capacitively coupled to the conducting 2DEG channel (13) via displacement currents (15). The electrical metallizations (14) are made of metal stacks, such as Cr/Au, Ti/Au, Ti/W, Cr/Al and Ti/Al. The Cr or Ti layers of the metal stack is, for example, of about 5-10 nm thickness, while the second metal layer, such as Au, W and Al, is of about 100-400 nm thickness. The actual metallizations (14) are chosen according to the established technology and assembly line at a particular clean room fabrication facility.

In yet further embodiment, substrate layer (10) comprises a suitable material for forming the barrier layer and is composed, for example, of sapphire, silicon, silicon carbide, gallium nitride or aluminium nitride. The hetero-junction structure (11, 12) is deposited on the substrate layer (10), for example, by a method of metalorganic chemical vapour deposition (MOCVD), and forms a two-dimensional electron gas (2DEG) channel (13) in the close proximity to the interface between the buffer layer (11) and the barrier layer (12). The barrier layer (12) then may be either recessed or grown as a thin layer between the non-ohmic source and drain contacts, thereby forming an open gate area. "Open gate area" of the PC-HEMT is defined as an area between the source and drain non-ohmic contacts of the transistor which is directly exposed to a conductive medium, such as liquid or gas capable of conducting current.

The specific thickness of the barrier layer (12) in the open gate area is achieved by either dry etching the semiconductor material of the layer (12), i.e. recessing layer in the open gate area with the etching rate of 1 nm per 1-2 min in a controllable process, or coating the buffer layer (11) in the open gate area with an ultrathin layer of the III-V semiconductor material. In order to increase the charge sensitivity of the transistor, the surface of the recessed ultrathin barrier layer is post-treated with plasma (chloride) epi-etch process. Consequently, the natively passivated surface is activated by the plasma etch to create an uncompensated (ionised) surface energy bonds or states, which are neutralized after MOCVD growing.

Figure 4A:
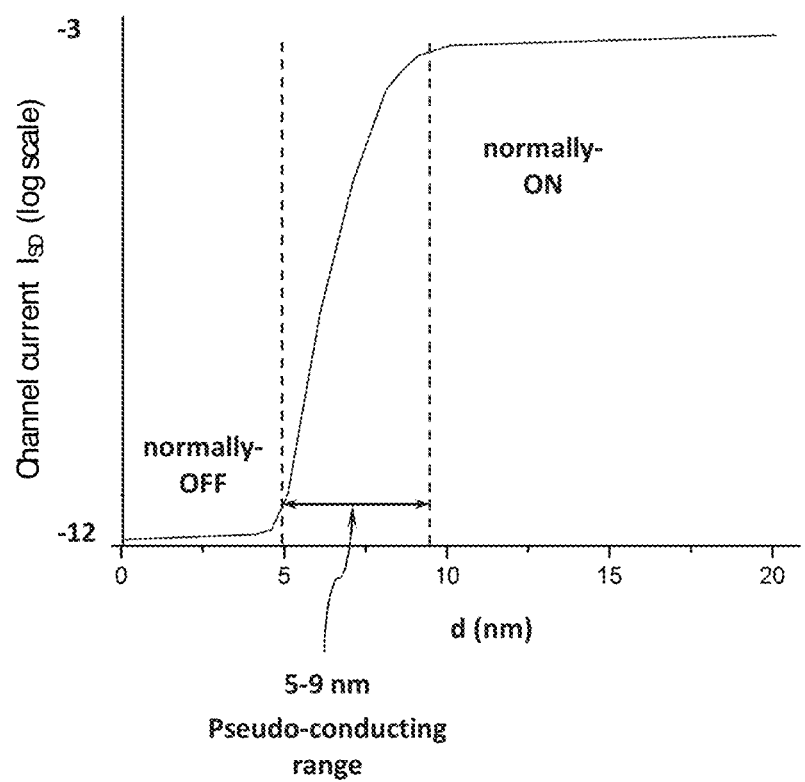
FIG. 4a schematically shows the dependence of the source-drain current (a charge carrier density) induced inside the 2DEG channel of a GaN/AlGaN HEMT on the thickness of the AlGaN barrier layer recessed in the open gate area.

FIG. 4 shows the dependence of the source-drain current (a charge carrier density) on the barrier layer thickness recessed in the open gate area. As seen from the plot, the HEMTs that have a thickness of the barrier layer in the open gate area larger than about 9 nm are normally-on devices. In such devices, the inherent macroscopic spontaneous polarisation effects present in the ionic bonds of III-V materials, a thin sheet of charges is induced at the top and bottom of the interfaces of the barrier layer, thereby forming the 2DEG layer. In other words, once a high electric field is induced in the barrier layer, the surface donor states at the top interface start donating electrons to form the 2DEG channel at the proximity of the hetero-junction interface without the application of a gate bias. These HEMTs are therefore normally-on devices. On the other hand, the HEMTs that have a thickness of the barrier layer in the open gate area lower than about 5 nm act as normally-off devices.

The barrier layer recessed or grown in the open gate area to 5-9 nm is optimised for significantly enhancing sensitivity of the PC-HEMT sensor. This specific thickness of the barrier layer in the open gate area corresponds to the "pseudo-conducting" current range between normally-on and normally-off operation modes of the transistor and requires further explanation.

"Pseudo-contacting" current range of the HEMT is defined as an operation range of the HEMT between its normally-on and normally-off operation modes. "Trap states" are states in the band-gap of a semiconductor which trap a carrier until it recombines. "Surface states" are states caused by surface reconstruction of the local crystal due to surface tension caused by some crystal defects, dislocations, or the presence of impurities. Such surface reconstruction often creates "surface trap states" corresponding to a surface recombination velocity. Classification of the surface trap states depends on the relative position of their energy level inside the band gap. The surface trap states with energy above the Fermi level are acceptor-like, attaining negative charge when occupied. However, the surface trap states with energy below the Fermi level are donor-like, positively charged when empty and neutral when occupied. These donor-like surface trap states are considered to be the source of electrons in the formation of the 2DEG channel. They may possess a wide distribution of ionization energies within the band gap and are caused by redox reactions, dangling bonds and vacancies in the surface layer. A balance always exists between the 2DEG channel density and the number of ionised surface donors which is governed by charge neutrality and continuity of the electric field at the interfaces.

Thus, the donor-like surface traps at the surface of the barrier layer of the HEMT are one of the most important sources of the 2DEG in the channel. However, this only applies for a specific barrier layer thickness. In a relatively thin barrier layer, the surface trap state is below the Fermi level. However, as the barrier layer thickness increases, the energy of the surface trap state approaches the Fermi energy until it coincides with it. The thickness of the barrier layer corresponding to such situation is defined as "critical". At this point, electrons filling the surface trap state are pulled to the channel by the strong polarisation-induced electric field found in the barrier to form the 2DEG instantly.

If the surface trap states are completely depleted, further increase in the barrier layer thickness will not increase the 2DEG density. Actually, if the 2DEG channel layer fails to stretch the barrier layer, the later will simply relax. Upon relaxation of the barrier layer, crystal defects are created at the interface between the buffer and barrier layers, and the piezoelectric polarisation disappears causing deterioration in the 2DEG density.

Figure 4B:
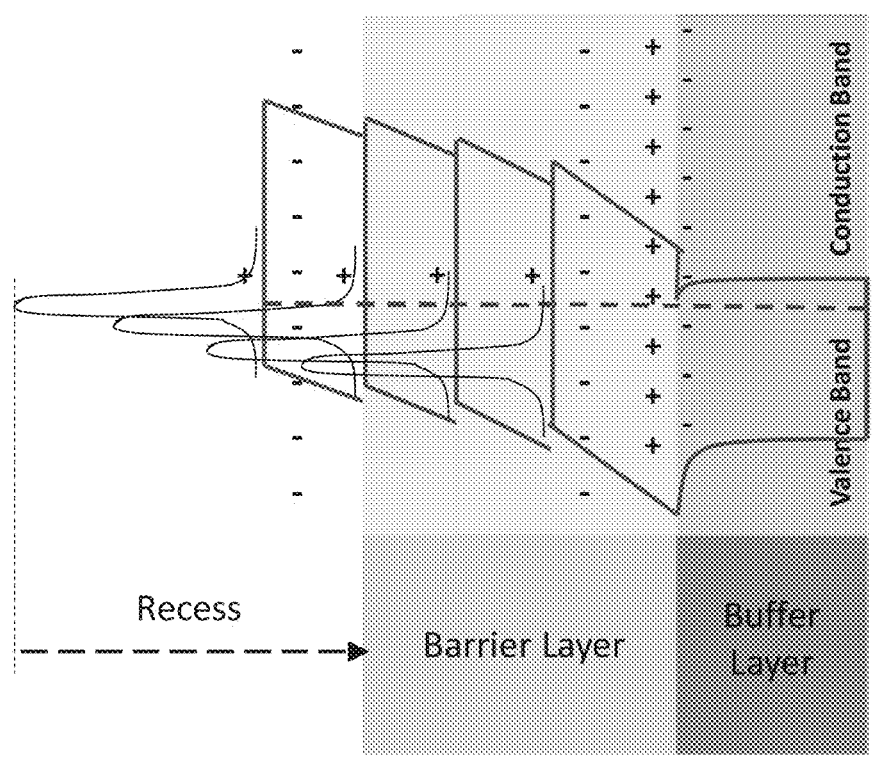
FIG. 4b illustrates a theory behind the 2DEG formation (charge neutrality combined with the lowest energy level) at the conduction band discontinuity.

In order to illustrate the above phenomenon of pseudo-conducting current, reference is now made to the following figures. As mentioned above, FIG. 4a shows the dependence of the source-drain current (a charge carrier density) on the recessed AlGaN barrier layer thickness. An energy equilibrium between the donor surface trap states and the AlGaN tunnel barrier leads to the 2DEG formation (charge neutrality combined with the lowest energy level) at the conduction band discontinuity. As explained above, decrease in the thickness of the barrier layer results in increase of the energy barrier. As a result, the ionisable donor-like surface trap states, which are responsible for electron tunnelling from the surface to 2DEG, drift bellow the Fermi level, thereby minimizing the electron supply to the 2DEG channel. This theoretical situation is illustrated in FIG. 4b. Therefore, the recess of the AlGaN layer from 9 nm to 5 nm leads to extremely huge drop in the 2DEG conductivity for six orders of magnitude.

In view of the above, it is clear that the mechanism of the 2DEG depletion based on recessing the barrier layer is strongly dependent on the donor-like surface trap states (or total surface charge). As the thickness of the barrier layer decreases, less additional external charge is needed to apply to the barrier layer surface in order to deplete the 2DEG channel. There is a critical (smallest) barrier thickness, when the 2DEG channel is mostly depleted but still highly conductive due to a combination of the energy barrier and the donor surface trap states energy. At this critical thickness, even the smallest energy shift at the surface via any external influence, such as surface reaction, charging etc., leads immediately to very strong 2DEG depletion. As a result, the surface of the barrier layer at this critical thickness is extremely sensitive to any smallest change in the electrical field of the surroundings.

Thus, the recess of the gate area of the barrier layer from 9 nm down to 5 nm significantly reduced the 2DEG density, brought the transistor to the "near threshold" operation and resulted in highly increased surface charge sensitivity. The specific 5-9 nm thickness of the barrier layer responsible for the pseudo-conducting behaviour of the transistor gives the sensor an incredible sensitivity. So, when it comes into a contact with an ionic fluid or body skin, it opens up the gate to be able to do the ultrasensitive sensing.

The top layer is recessed to this specific thickness after subjecting to short plasma activation by an ultra-low damage reactive-ion etching technique using inductively-coupled plasma (ICP) with a narrow plasma-ion energy distribution. Such short plasma treatment allows much lower roughness of the surface, which is a function of the semiconductor vertical damage depth during the plasma etching process. Such low surface roughness (about 0.2 nm and less) can be achieved only via this ICP-RIE ultra low damage etching process with a narrow plasma-ion energy distribution, and this inherently results in a very low vertical damage depth to the top layer, which allows the minimal surface scattering and minimal surface states-2DEG channel interaction with the maximum signal-to-noise ratio of the sensor. Thus, the depth effect of the vertical sub-nanometre damage to the top recessed layer, due to an ultra-low damage ICP-RIE etching process with a very narrow plasma-ion energy distribution, is the only way to optimally achieve the required sub-nanometre roughness of the semiconductor surface. This inherently results in an adjustable pseudo-conductive working point with the highest charge sensitivity ever possible. This depth effect is always inherent to the sub-nanometre roughness of the semiconductor surface, which was measured using AFM (atomic force microscope).

Thus, in addition to the recessed top layer thickness, roughness of the top layer surface is another very important parameter that has not been previously disclosed. It has been surprisingly found that the roughness of the top layer surface (in the open gate sensitive area) bellow 0.2 nm prevents scattering of the donor-like surface trap states. Thus, the combination of these two features: 5-9 nm thickness of the top layer in the open gate area and strongly reduced roughness of its surface make the PC-HEMT an incredibly strong functional amplifier.

In a certain aspect, the method for manufacturing of the PC-HEMTs of the present invention comprises the following steps:

Step 1: Plasma-enhanced atomic layer deposition (ALD) of alumina ($Al_2O_3$) on a pre-aligned masked Si—GaN/AlGaN wafer with nitrogen-plasma de-trapping for the thickness of the $Al_2O_3$ layer being 3-10 nm. The $Al_2O_3$ layer thickness was measured with an X-ray reflectometer.

Step 2: Plasma-enhanced atomic layer deposition (ALD) pattering of the wafer coated with the thin $Al_2O_3$ layer in Step 1, with hydrogen fluoride (HF) or using the aforementioned reactive-ion etching (RIE) technique.

Step 3: Optionally creating the source and drain ohmic contacts (in case ohmic contacts are required) on the coated wafer obtained in Step 2 from metal stacks, for example Ti/Al/Mo/Au, Ti/Al/Ni/Au, Ti/Au and Ti/W, having 15-50 nm thickness, using spin-coating technique or e-beam physical vapour deposition (VPD) of the stack metals. The deposition rates using the e-VPD technique were determined for the ohmic-stack metals using the Dektak Profilometer with dummy lift-off samples.

Step 4: Two-dimensional electron gas (2DEG) channel-pattering of the wafer obtained in Step 3 with argon- or nitrogen-ion implantation.

Step 5: Plasma-enhanced chemical vapour deposition (CVD) of the ONO stack over the wafer obtained in Step 4. This is the stress-free technique to deposit the layer of the SiO—SiN—SiO stack having an exemplary thickness of about 200-300 nm and structured by the ICP-RIE dry etching, which is the CF4-based etching method. In this step, the pseudo-conducting channel areas and ohmic electrical contact pads of the transistor become available.

Step 6: Optional lift-off deposition of an Au or Ti/W-CMOS-gate electrode (in case a gate electrode is to be deposited on the top layer of the heterojunction structure for an integrated MMIC-HEMT-based amplifier manufacturing).

Step 7: Optional plasma-enhanced ALD pattering with RIE or HF above sensing area (in case the plasma-enhanced ALD layer deposited in Step 1 is removed separately to ONO stack).

Step 8: Atomic layer etching (ALE) of the wafer obtained in Steps 5-7. This sophisticated technique carried out in the clean manufacturing cluster of the applicant is the only technique allowing the removal of individual atomic layers (the top atomic layers of the wafer). ALE is a way better-controlled technique than RIE, though it has not been commercially used until now because very sophisticated gas handling is required, and removal rates of one atomic layer per second are the real state of the art. This step is the step of creating the pseudo-conducting working point of the transistor, because ALE allows achieving the specific thickness of 5-9 nm thickness of the top layer in the open gate area with the extremely low surface roughness of the top layer below 0.2 nm.

Step 9: Optional plasma-enhanced CVD or ALD of the dielectric layer used for device passivation and in some gas sensors.

Step 10: Optional deep reactive-ion etching (DRIE or Bosch process) of the Si-substrate under sensing areas (in case the substrate is on the free-standing membranes—used, for example, in RF-HEMTs, FBAR and SAW sensors).

Figure 5A:
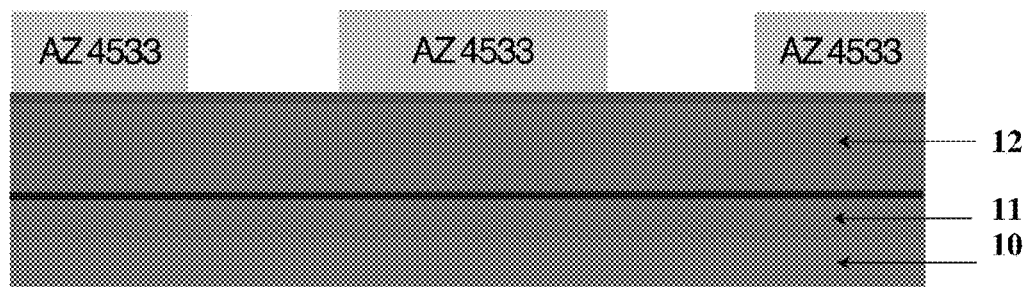
FIG. 5a schematically shows the 2DEG area created in the step of the 2DEG-pattering via ion implantation during the manufacturing process. AZ 4533 is a positive thick resist.
Figure 5B:
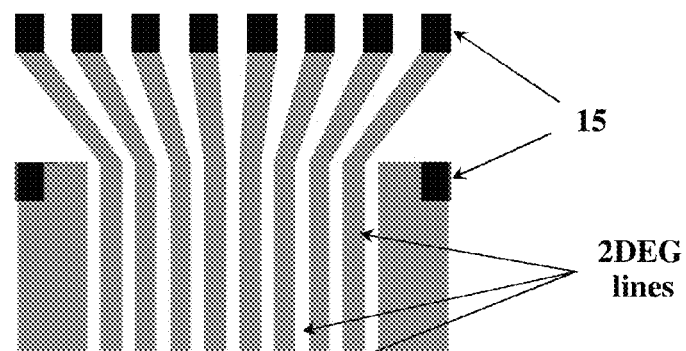
FIG. 5b shows the lithographic mask of the sensor layout of the present invention.
Figure 5C:
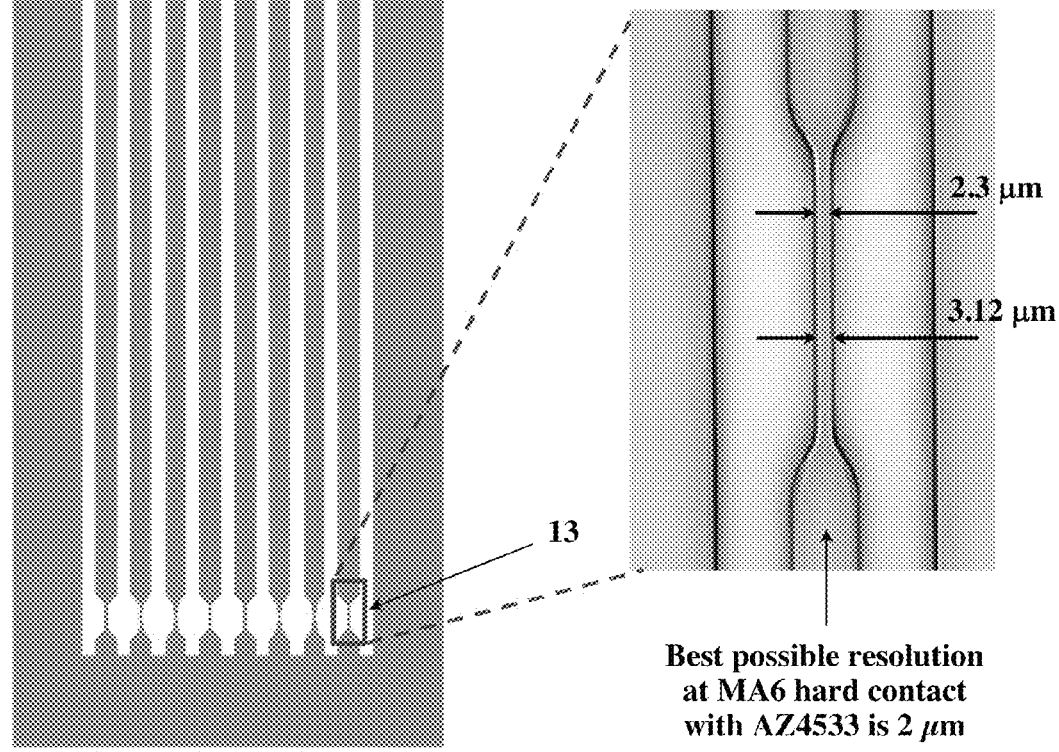
FIG. 5c shows the lithographic image of the 2DEG channel formed with AZ 4533 thick resist lithography over the mask shown in FIG. 5b.

Reference is now made to FIGS. 5a-5c showing the sensor, which is obtained in Step 4 of the 2DEG-channel pattering. The lithography of the sensor was performed with AZ 4533, which is a positive thick resist having optimised adhesion for common wet etching. The lithographic resist film thickness obtained at 7000-rpm spin speed and at 100° C. for 1 min was 3 μm. Thus, as seen in the lithographic image of FIG. 5c, the formed 2DEG channel (13) is approximately 2-3 μm wide. The overall exposure time was 9 sec, followed by 5-min development in MIF726 developer.

Figure 5F:
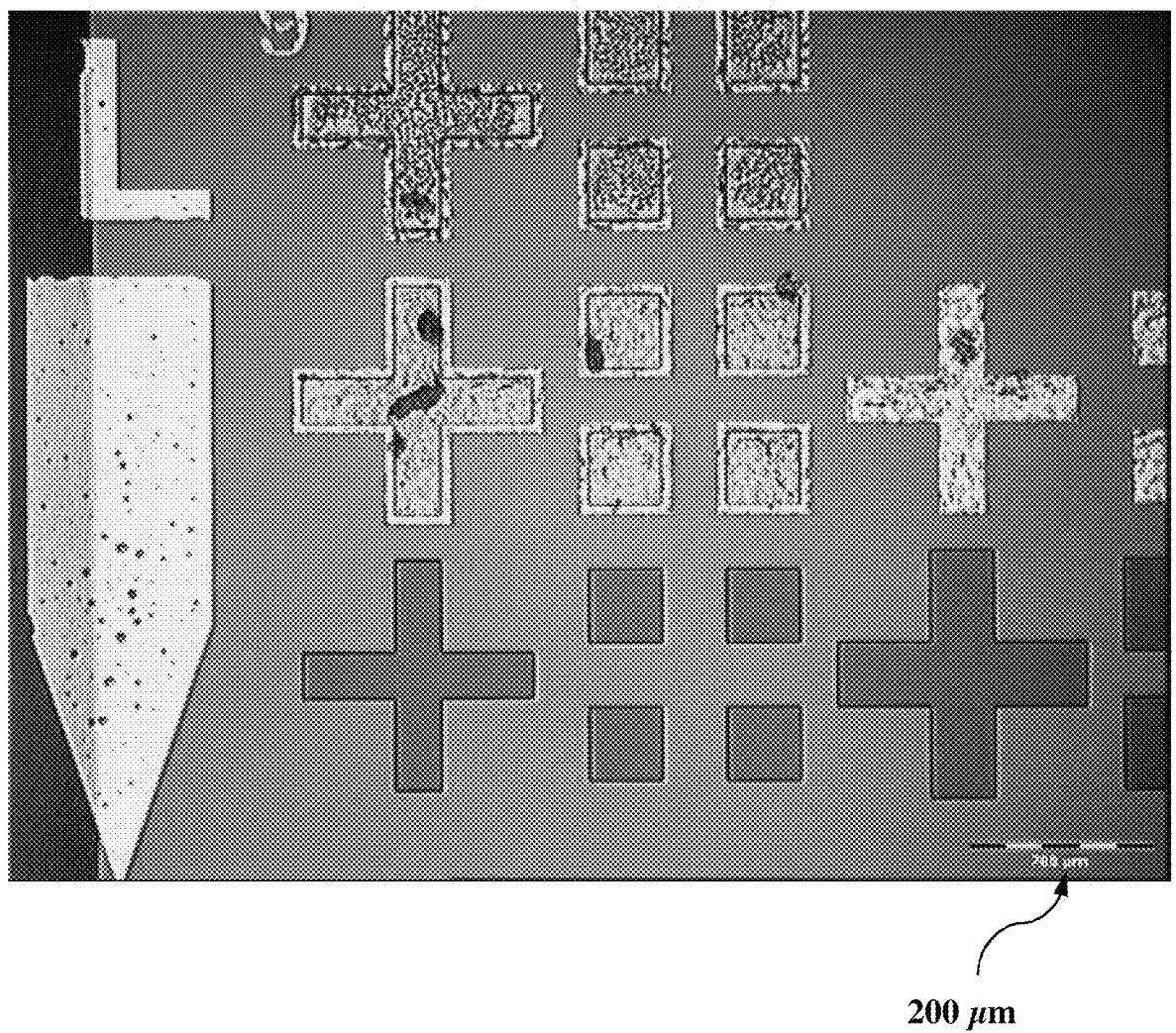
FIG. 5f shows the ±2-μm alignment precision on 25×25 mm² samples in the lithography of the sensor layout of the present invention.
Figure 5G:
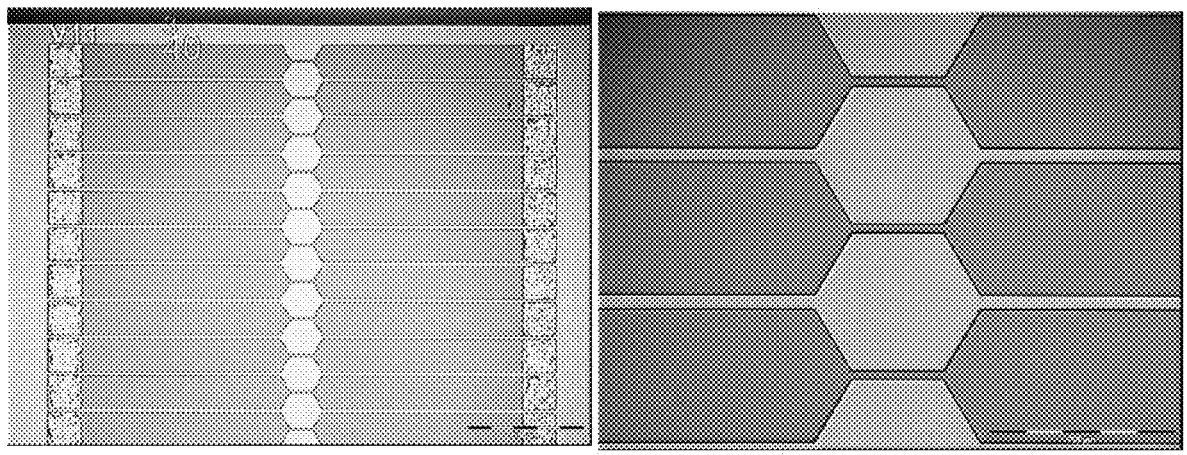
FIG. 5g shows the lithographic images of the multichannel samples.
Figure 5G:
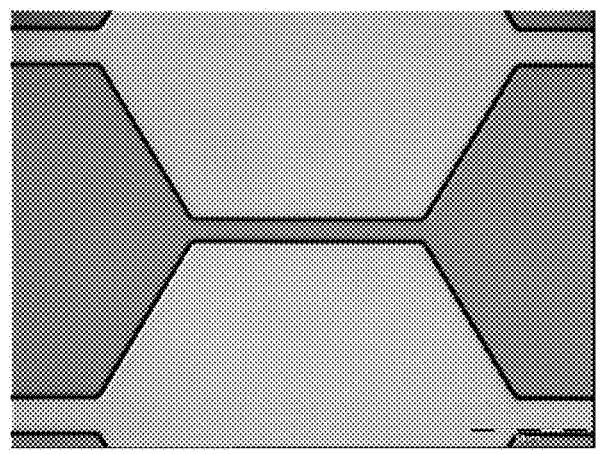
Figure 5H:
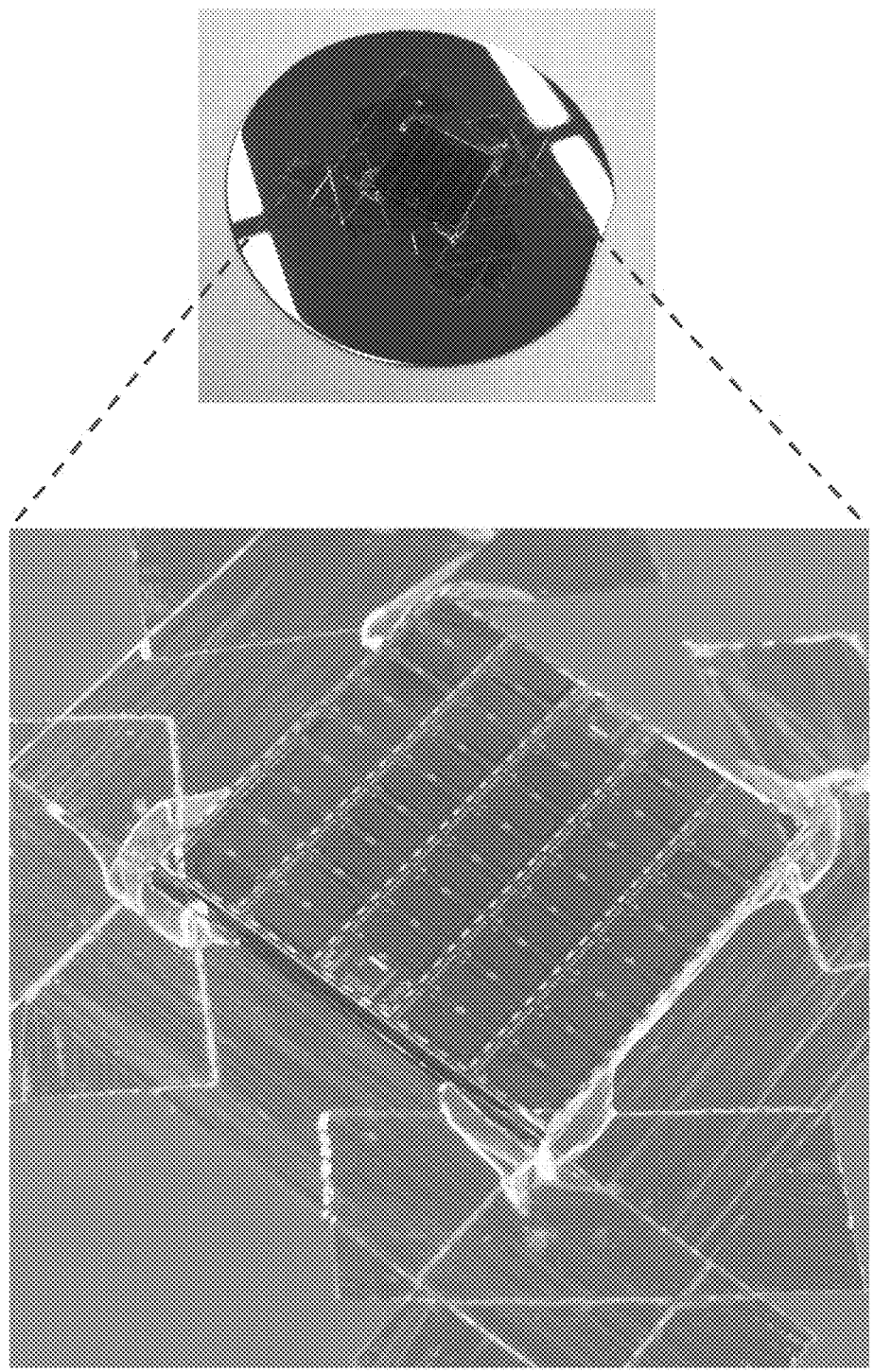
FIG. 5h shows the fixed sample on the Si—GaN/AlGaN wafer prepared for ion implantation and containing around 30-32 sensors with 4-8 channels on each sample.

FIG. 5d-5e show the mask and corresponding lithographic image, respectively, of the sensor layout of the present invention. FIG. 5f demonstrates the high alignment precision of ±2-μm on 25×25 mm² samples in the lithography of the sensor layout of the present invention. FIG. 5g shows the lithographic images of the multichannel samples. FIG. 5h shows the fixed sensor chip sample on the Si—GaN/AlGaN wafer, which contains approximately 30-32 sensors with 4-8 channels on each sample and prepared for ion implantation. FIG. 5i shows the obtained lithographic image of the present sensor layout with the AZ4533 resist after development, prepared for ion implantation. FIG. 5j shows the 2DEG channels (dark) patterned by ion-implantation after the resist removal. The argon-ion implantation was conducted with 20 keV and 30 keV energies and with an exemplary dose of $2.5e^{13}/cm^2$ and a 7° tilt angle. AZ4533 was removed with oxygen plasma at 220 W for 10 min. FIG. 5k shows the visible non-implanted area containing the conductive 2DEG channel.

The atomic layer etching (ALE) performed in Step 8 of the manufacturing process is the most important stage in the process. As mentioned above, it allows the controlled recess of a top layer, removing a single atomic layer-by-layer, where the etch thickness is in the order of magnitude of a single atomic monolayer. As explained above, such ultra-low damage to the top layer of the heterogeneous structure, when the actual surface roughness is controlled by a single atomic monolayer, allows to achieve the sub-nanometre roughness (about 0.2 nm and less) of the top layer when its thickness is only few nanometres (5-9 nm).

The ALE process sequence consists of repeated cycling of process conditions. The total amount of material removed is determined by the number of repeated cycles. Each cycle is typically comprised of four steps: adsorption, first purge, desorption and second purge. During the adsorption step of the cycle, reactive species are generated in the reactor (for example, upon plasma excitation), adsorbed by, and react with material on the wafer. Due to the self-limiting process, and with the proper choice of reactants and process conditions, reaction takes place with only a thin layer of material, and the reaction by-products are formed. This step is followed by purging of the reactor to remove all traces of the reactant. Then the by-product desorption takes place due to bombardment of the wafer surface by noble gas ions with a tightly controlled energy. Again, by-products are purged from the reactor, and the wafer is ready for the last two (optional) steps of the manufacturing process.

Figure 6A:
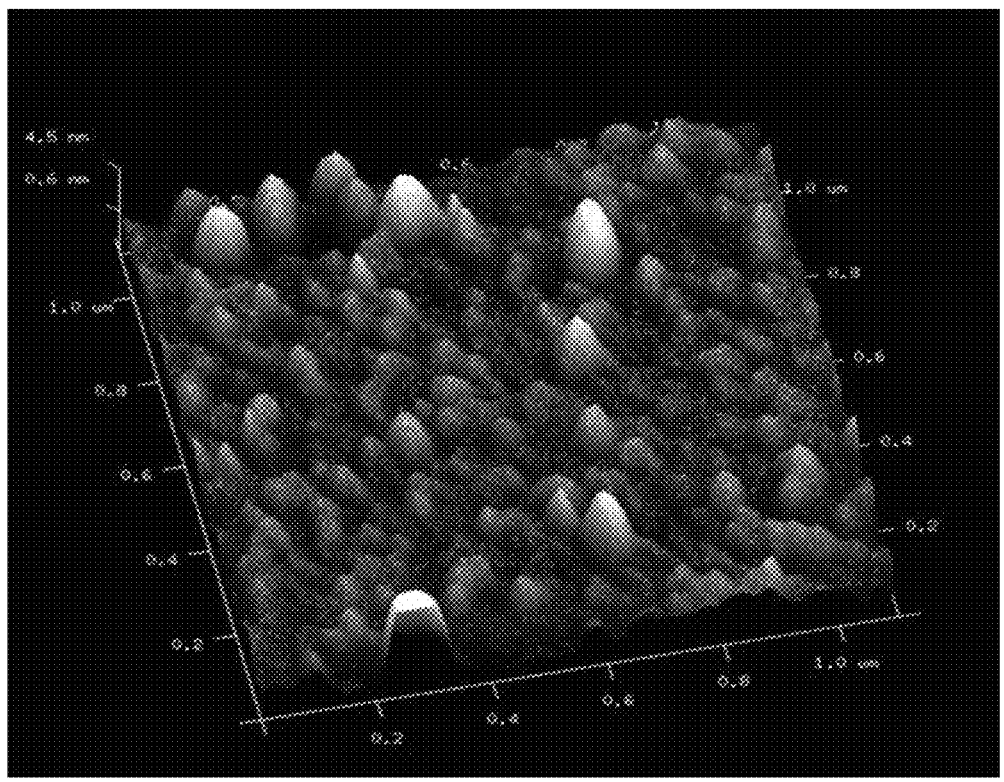
FIG. 6a shows the AFM surface image of the top recessed layer of the PC-HEMT made by the manufacturing process of the present invention. The measured RMS value of the surface roughness is 0.674 nm in this case.
Figure 6B:
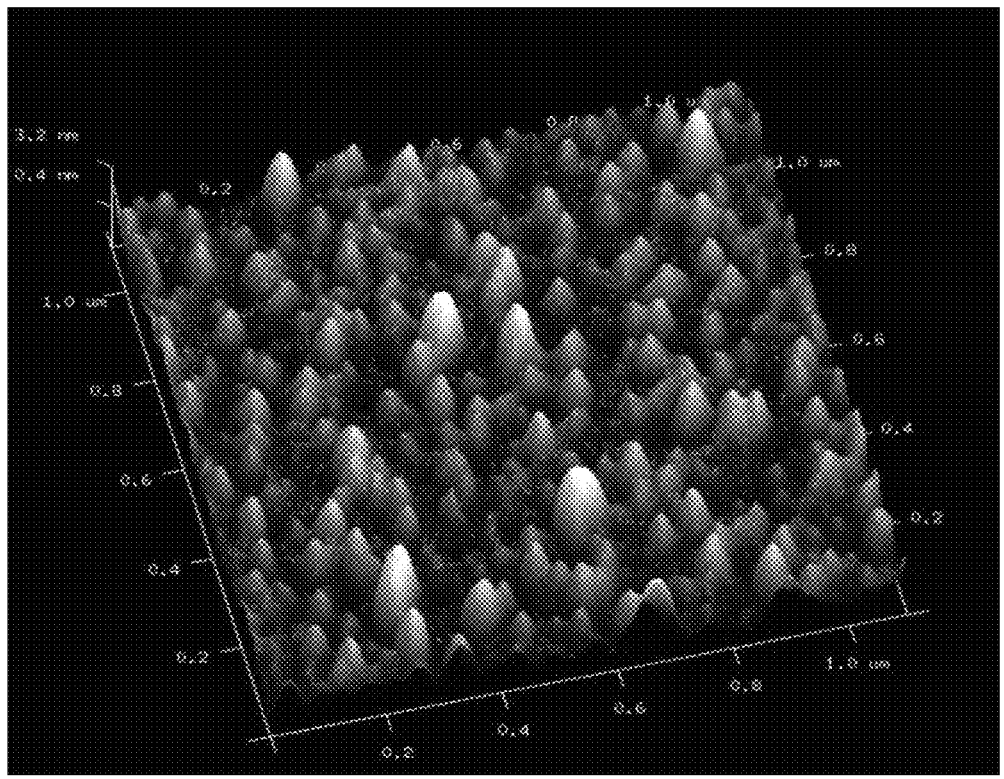
FIG. 6b shows the AFM surface image of the top recessed layer of the HEMT made by a conventional manufacturing process. The measured RMS value of the surface roughness is 1.211 nm in this case.

Reference is now made to FIG. 6a showing the AFM image of the top recessed layer surface of the PC-HEMT produced by the manufacturing process of the present invention. The measured RMS value of the surface roughness is 0.674 nm in this case. FIG. 6b shows the AFM surface image of the top recessed layer of the HEMT made by a conventional manufacturing process. In this conventional process, the HEMT initially had a top ultrathin-grown AlGaN layer of the 6-7 nm thickness. This layer was recessed with inductively-coupled plasma (ICP) for 60 sec using a conventional reactive-ion etching (ME) technique. The measured RMS value of the surface roughness is 1.211 nm in this case. FIG. 6c show the time-dependent plot of the drain-source electric current $I_{DS}$ of the nitrogen oxide sensor measuring 100 ppb of the $NO_2$ gas in 80%-humid air, where the sensor incorporates the PC-HEMT made by the manufacturing process of the present invention. FIG. 6d show the time-dependent plot of the $I_{DS}$ of the nitrogen oxide sensor measuring 100 ppb of the $NO_2$ gas in 80%-humid air, where the sensor incorporates and based on the HEMT made by the conventional manufacturing process. It is clear from these comparative examples that the manufacturing process of the present invention based on the ultra-low damaging RIE with a narrow plasma-ion energy distribution leads to much lower roughness of the semiconductor surface, which in turn leads to incredibly high sensitivity of the sensor, which is demonstrated in the present invention.

In a further aspect, the hetero-junction structure may be a three-layer structure consisting of two buffer layers and one barrier layer squeezed between said buffer layers like in a sandwich, wherein the top layer is a buffer layer. This may lead to formation of the two-dimensional hole gas (2DHG) in the top buffer layer above the barrier layer which results in reversing polarity of the transistor compared to the two-layer structure discussed above.

In general, polarity of III-V nitride semiconductor materials strongly affects the performance of the transistors based on these semiconductors. The quality of the wurtzite GaN materials can be varied by their polarity, because both the incorporation of impurities and the formation of defects are related to the growth mechanism, which in turn depends on surface polarity. The occurrence of the 2DEG/2DHG and the optical properties of the hetero-junction structures of nitride-based materials are influenced by the internal field effects caused by spontaneous and piezo-electric polarizations. Devices in all of the III-V nitride materials are fabricated on polar {0001} surfaces. Consequently, their characteristics depend on whether the GaN layers exhibit Ga-face positive polarity or N-face negative polarity. In other words, as a result of the wurtzite GaN materials polarity, any GaN layer has two surfaces with different polarities, a Ga-polar surface and an N-polar surface. A Ga-polar surface is defined herein as a surface terminating on a layer of Ga atoms, each of which has one unoccupied bond normal to the surface. Each surface Ga atom is bonded to three N atoms in the direction away from the surface. In contrast, an N-polar surface is defined as a surface terminating on a layer of N atoms, each of which has one unoccupied bond normal to the surface. Each surface N atom is also bonded to three Ga atoms in the direction away from the surface. Thus, the N-face polarity structures have the reverse polarity to the Ga-face polarity structures.

As described above for the two-layer heterojunction structure, the barrier layer is always placed on top of the buffer layer. The layer which is therefore recessed is the barrier layer, specifically the AlGaN layer. As a result, since the 2DEG is used as the conducting channel and this conducting channel is located slightly below the barrier layer (in a thicker region of the GaN buffer layer), the hetero-junction structure is grown along the {0001}-direction or, in other words, with the Ga-face polarity. However, as explained above, the physical mechanism that leads to the formation of the 2DEG is a polarisation discontinuity at the AlGaN/GaN interface, reflected by the formation of the polarisation-induced fixed interface charges that attract free carriers to form a two-dimensional carrier gas. It is a positive polarisation charge at the AlGaN/GaN interface that attracts electrons to form 2DEG in the GaN layer slightly below this interface.

As noted above, polarity of the interface charges depends on the crystal lattice orientation of the hetero-junction structure, i.e. Ga-face versus N-face polarity, and the position of the respective AlGaN/GaN interface in the hetero-junction structure (above or below the interface). Therefore, different types of the accumulated carriers can be present in the hetero-junction structure of the embodiments.

In case of the three-layer hetero-junction structure, there are four possible configurations:

Ga-Face Polarity
1) The Ga-face polarity is characterised by the 2DEG formation in the GaN layer below the AlGaN barrier layer. This is actually the same two-layer configuration as described above, but with addition of the top GaN layer. In this configuration, the AlGaN barrier layer and two GaN buffer layers must be nominally undoped or n-type doped.
2) In another Ga-face configuration shown in FIG. 7a, in order to form the conducting channel comprising a two-dimensional hole gas (2DHG) in the top GaN layer above the AlGaN barrier layer in the configuration, the AlGaN barrier layer should be p-type doped (for example, with Mg or Be as an acceptor) and the GaN buffer layer should be also p-type doped with Mg, Be or intrinsic.

N-Face Polarity
3) The N-face polarity is characterised by the 2DEG formation in the top GaN layer above the AlGaN barrier layer, as shown in FIG. 7b. In this case, the AlGaN barrier layer and two GaN buffer layers must be nominally undoped or n-type doped.
4) The last configuration assumes that the 2DHG conducting channel is formed in the buffer GaN layer below the AlGaN barrier layer. The top GaN layer may be present (three-layer structure) or not (two-layer structure) in this case. The AlGaN barrier layer must be p-type doped (for example with Mg or Be as an acceptor) and the bottom GaN layer should be also p-type doped with Mg, Be or intrinsic.

Thus, there are four hetero-junction three-layer structures implemented in the transistor of the embodiments, based on the above configurations:
A. Ga-Face GaN/AlGaN/GaN heterostructure with the 2DEG formed in the GaN buffer layer below the AlGaN barrier layer. In this case, the top GaN layer may be omitted to obtain the two-layer structure. For the three-layer structure, the top GaN layer must be recessed to 1-9 nm thickness in the open gate area or grown with this low thickness, with the roughness below 0.2 nm, and the thickness of the AlGaN barrier can be adjusted properly during growth.
B. Ga-Face GaN/AlGaN/GaN heterostructure with the 2DHG conducting channel formed in the top GaN layer above the AlGaN barrier layer. The top GaN layer must be recessed to 5-9 nm thickness in the open gate area with the roughness below 0.2 nm, and the thickness of the AlGaN barrier layer can be adjusted properly. P-type doping concentrations of the GaN layer and AlGaN barrier have to be adjusted; the 2DHG has to be contacted (in the ideal case by ohmic contacts).
C. N-Face GaN/AlGaN/GaN heterostructure with the 2DEG in the top GaN layer above the AlGaN barrier layer. The top GaN layer must be recessed to 5-9 nm thickness in the open gate area with the roughness below 0.2 nm. Thickness of the AlGaN barrier can be adjusted during growth.

N-type doping levels of the GaN buffer layer and the AlGaN barrier layer must be adjusted; the 2DEG has to be contacted (in the ideal case by ohmic contacts).

D. N-Face GaN/AlGaN/GaN heterostructure with the 2DHG in the GaN buffer layer below the AlGaN barrier layer. In this case, the top GaN layer may be omitted to obtain the two-layer structure. In both, the two-layer and three-layer configurations, the top GaN layer must be recessed to 1-9 nm thickness in the open gate area with the roughness below 0.2 nm, and the thickness of the AlGaN barrier can be adjusted properly.

Figure 7C:
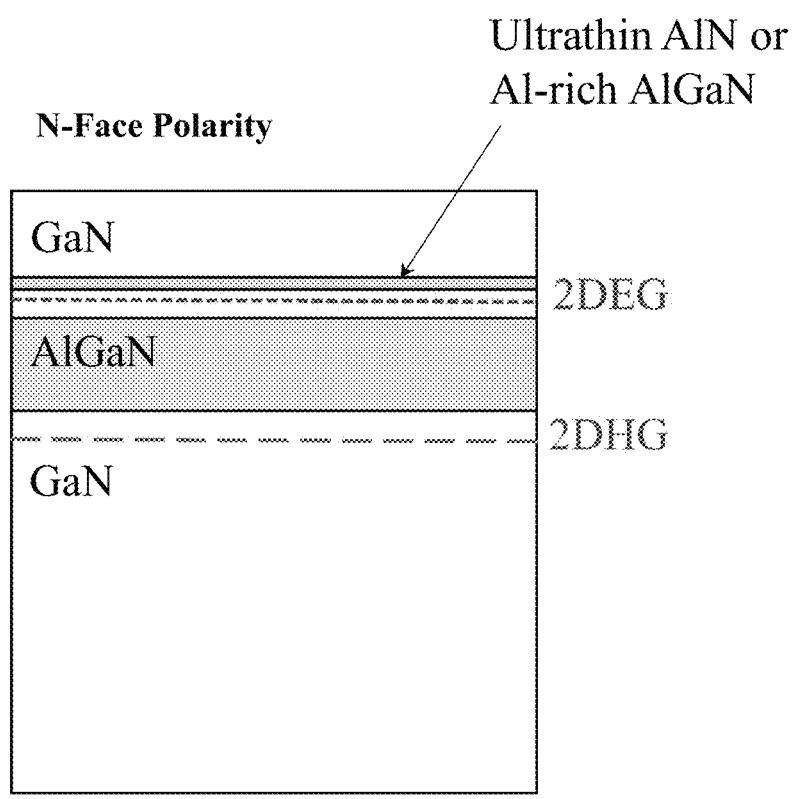
FIG. 7c schematically shows the formation of the 2DEG conducting channel in the N-face three-layer GaN/AlGaN/GaN PC-HEMT structure with an ultrathin Al(GaN)N layer for improved confinement.

In all the above structures, the deposition of a dielectric layer on top might be beneficial or even necessary to obtain a better confinement (as in case of the N-face structures). As shown in FIG. 7c, for the above "C" structure, it may be even more beneficial to include an ultrathin (about 1 nm) AlN or AlGaN barrier layer with high Al-content on top of the 2DEG channel to improve the confinement.

The preferable structures of the embodiments are structures "B" and "C". In the structure "B", the 2DHG conducting channel formed in the top GaN layer, which has a higher chemical stability (particularly towards surface oxidation) than the AlGaN layer. Concerning the structure "C", the 2DEG conducting channel might be closer to the surface. Therefore, the electron mobility might be lower than in the 2DEG structure with the Ga-face polarity. In general, the polarity of the heterostructure can be adjusted by the choice of the substrate (e.g. C-face SiC) or by the growth conditions.

Vitushinsky et al (2013) has recently proved the above concept of pseudo-conducting by demonstrating that recessing the AlGaN layer of the AlGaN/GaN heterostructures in the open gate area can dramatically enhance the sensitivity of the HEMT to surface interactions. They investigated the response to ppb levels of $NO_2$ in humid conditions and showed that when the AlGaN barrier layer is relatively thick (22 nm), the heterojunction 2DEG surface charge sensitivity is around six orders of magnitude smaller compared to 6.3 nm AlGaN barrier (in case of $NO_2$ surface effect). Recess of the gate area of the barrier layer down to 6.3 nm significantly reduced the 2DEG density, brought the HEMT to the "near threshold" operation and resulted in strongly increased sensitivity.

Thus, the AlGaN/GaN structures forming the 2DEG channel at their interfaces can be used as a generic platform for the ultrasensitive detection of gases because of its robustness and intrinsic sensitivity to surface charge or dipoles. In humid conditions, the water layer on the AlGaN surface creates a positive surface charge and the surface polarity is altered, which strongly increases the conductivity of the 2DEG channel. This is because the changes in the polarisation or charge distribution at the AlGaN surface strongly affect the charge density in the 2DEG channel. Upon gas exposure, the positive surface charge is neutralized by the gas, leading to a decrease of the charge carrier density in the 2DEG channel. As a consequence, a tremendous decrease of the current through the 2DEG channel is observed. This phenomenon is used for ultralow-power continuous air quality monitoring at humidity levels higher than 10%. The extremely low current noise level in the AlGaN/GaN structures enables the reproducible detection of variations in the gas concentration of 1 ppb.

Figure 8A:
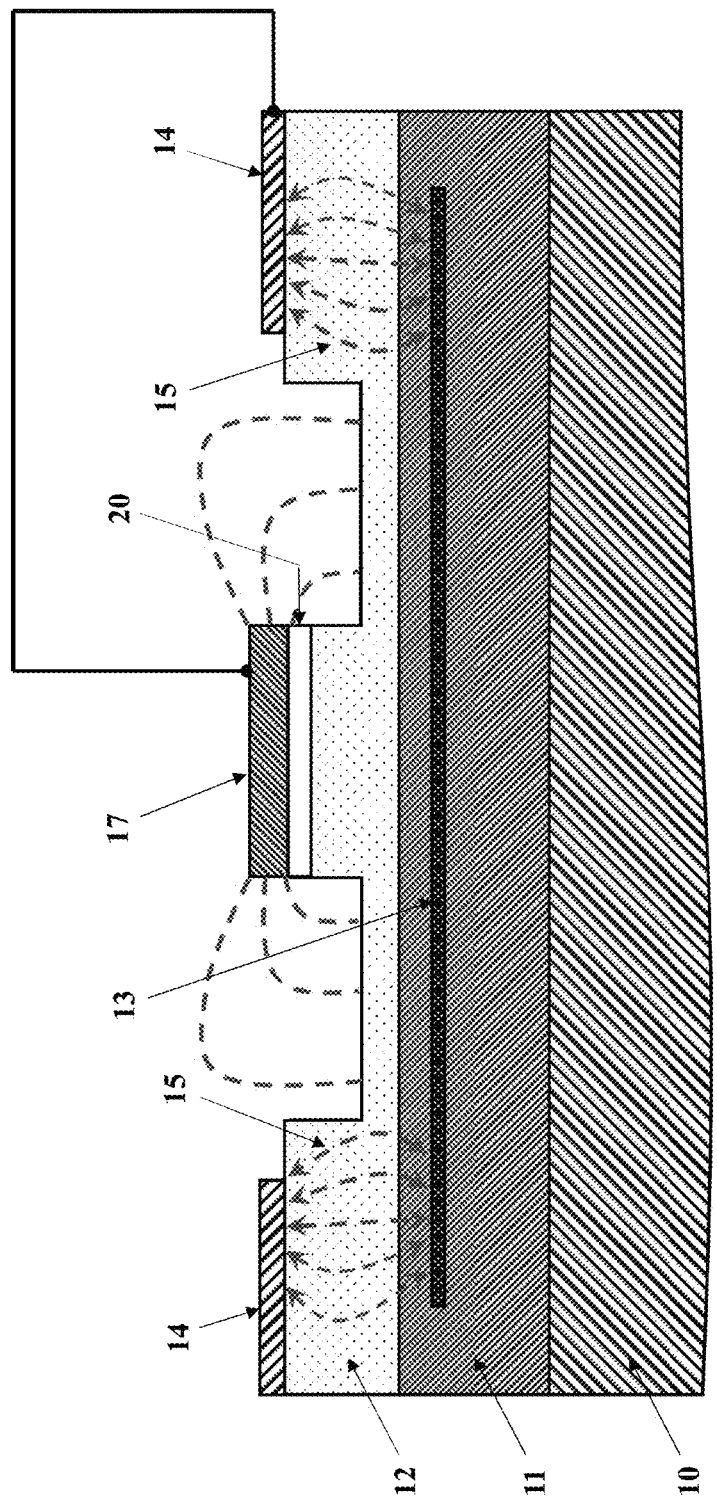
FIG. 8a schematically shows a cross-sectional view of the PC-HEMT of embodiments with a non-recessed AlGaN barrier layer and a metal gate electrode placed directly on said barrier layer.

In a further aspect of the present application, FIG. 8a shows a cross-sectional view of another configuration of the PC-HEMT of an embodiment of the present application comprising:

a multilayer hetero-junction structure made of III-V single-crystalline or polycrystalline semiconductor materials, said structure comprising at least one buffer layer (11) and at least one barrier layer (12), said layers being stacked alternately, and said structure being deposited on a substrate layer (10);

a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain non-ohmic contacts;

electrical metallizations (14) capacitively-coupled to said 2DEG or 2DHG channel (13) for inducing displacement currents (15), thereby creating non-ohmic source and drain contacts connecting said transistor to an electric circuit; and a metal gate electrode (17) placed directly on said barrier layer between said source and drain non-ohmic contacts and electrically connected to the source electrical metallization;

wherein:
 (i) the thickness (d) of said barrier layer (12) beneath said metal gate electrode (17) is about 5-9 nm which corresponds to the pseudo-conducting current range between normally-on and normally-off operation mode of the transistor, and
 (ii) the surface of said barrier layer (12) has a roughness of about 0.2 nm or less.

In the above configuration, the barrier layer (12), specifically AlGaN layer, is not recessed, and the dielectric layer (20) of about 1-10 nm thickness is deposited on the non-recessed barrier layer, followed by placing the metal gate electrode (17) on top of it. The metal gate electrode (17) thereby creates a hard mask for AlGaN recessing to the pseudo-conducting point and then exhibits a shadow gating effect to the open recessed areas. As a result, the charge trapping at the AlGaN/dielectric/metal interface is no longer affecting the recessed sensitive AlGaN area, and hence, the electrical leakage from the metal gate to the 2DEG channel is significantly decreased. This configuration is called a "shadow gate" configuration.

Figure 8B:
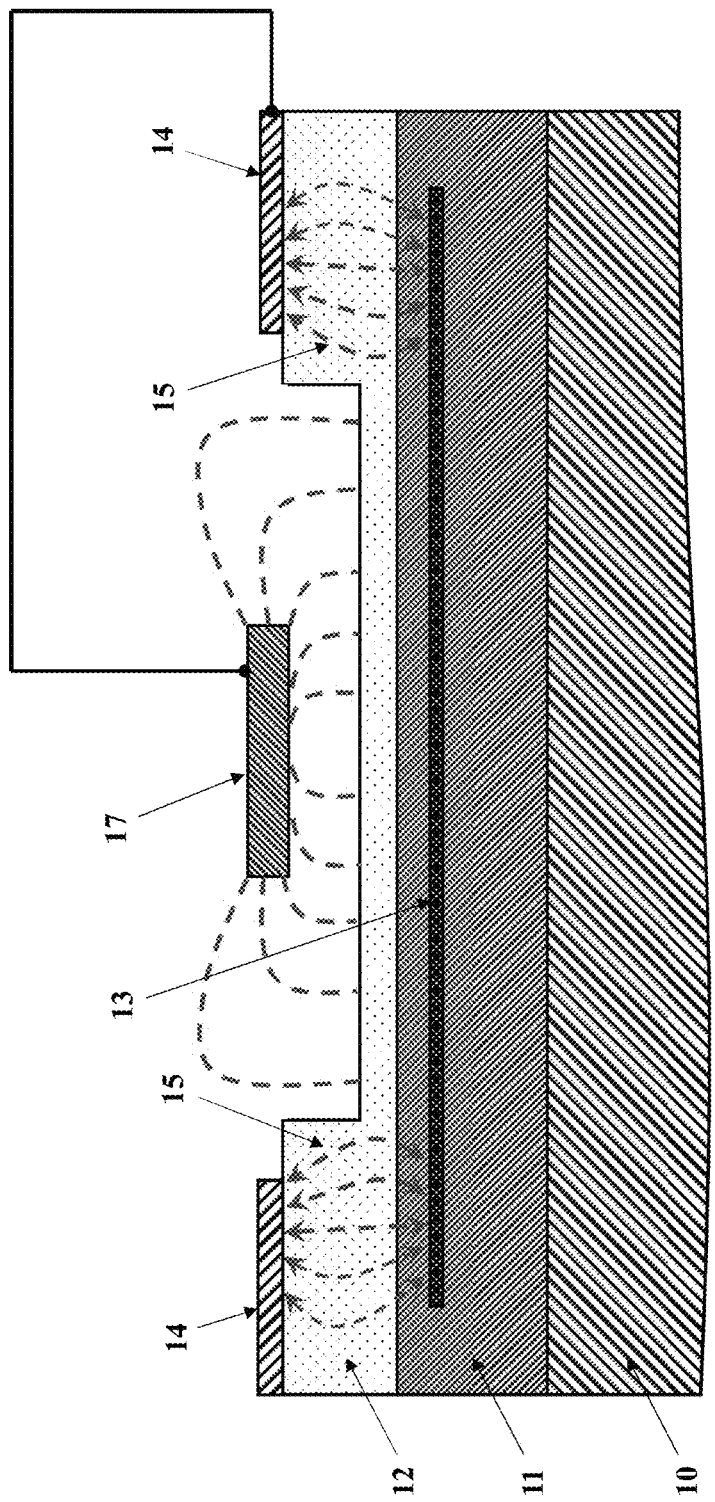
FIG. 8b schematically shows a cross-sectional view of the PC-HEMT of embodiments with a mechanically suspended metal gate.

Further, FIG. 8b shows a cross-sectional view of still another configuration of the PC-HEMT of an embodiment of the present application comprising:

a multilayer hetero-junction structure made of III-V single-crystalline or polycrystalline semiconductor materials, said structure comprising at least one buffer layer (11) and at least one barrier layer (12), said layers being stacked alternately, and said structure being deposited on a substrate layer (10);

a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain non-ohmic contacts;

electrical metallizations (14) capacitively-coupled to said 2DEG or 2DHG channel (13) for inducing displacement currents (15), thereby creating non-ohmic source and drain contacts connecting said transistor to an electric circuit; and a mechanically suspended metal gate electrode (17) placed above the barrier layer (12) between said non-ohmic source and drain contacts and electrically connected to the source electrical metallization;

wherein:
(i) the thickness (d) of said barrier layer (12) between said source and drain non-ohmic contacts is about 5-9 nm which corresponds to the pseudo-conducting current range between normally-on and normally-off operation mode of the transistor;
(ii) the surface of said barrier layer (12) has a roughness of about 0.2 nm or less; and
(iii) said metal electrode (17) has no physical contact with said barrier layer (12) beneath.

In the above configuration, the metal gate of the transistor is realised as a mechanically suspended gate structure placed directly above the recessed barrier layer, at the height of about 10-100 nm. This configuration prevents any electrical leakage normally occurring at the metal gate/barrier layer interface. The mechanically suspended gate electrode (17) is discharged via the connection to the source metallization. The connection can be high-ohmic and can be established via an optional capacitor to prevent the strong signal decay. This configuration is called a "suspended gate" configuration.

In addition, the connection of the suspended gate to the source metallization allows the fine tuning of the sensor gain by $V_{DS}$. The suspended metal gate electrode (17) may also be discharged from the parasitic charges via an additional opto-coupled electrode or using the AC-powered $V_{DS}$ and $V_{GS}$.

By applying a gate voltage $V_{GS}$, the pseudo-conductive 2DEG channel can be modulated according to an electrical field. As discussed above, gas molecules can create polarised dipoles or chemical compounds having dipole moments on the sensor surface. These specific dipole moments can be determined with an additional reference gating field from the gate electrode.

In a completely dry air, the PC-HEMT of the present embodiments is nearly in the normally-off state having a device current extremely small, due to a full depletion of the 2DEG channel through the surface trap states and small piezoelectric polarisation. However, if there is some humidity in air, a water layer is formed on the AlGaN surface inducing a positive space charge, which is equal to the effect of a positive gate potential, thereby strongly increasing the conductivity of the 2DEG channel. Therefore, in order to ensure the operation of the PC-HEMT in a dry environment, the AlGaN layer surface may be further coated with a functionalisation layer for binding gas molecules, which are desired to be detected.

Figure 9A:
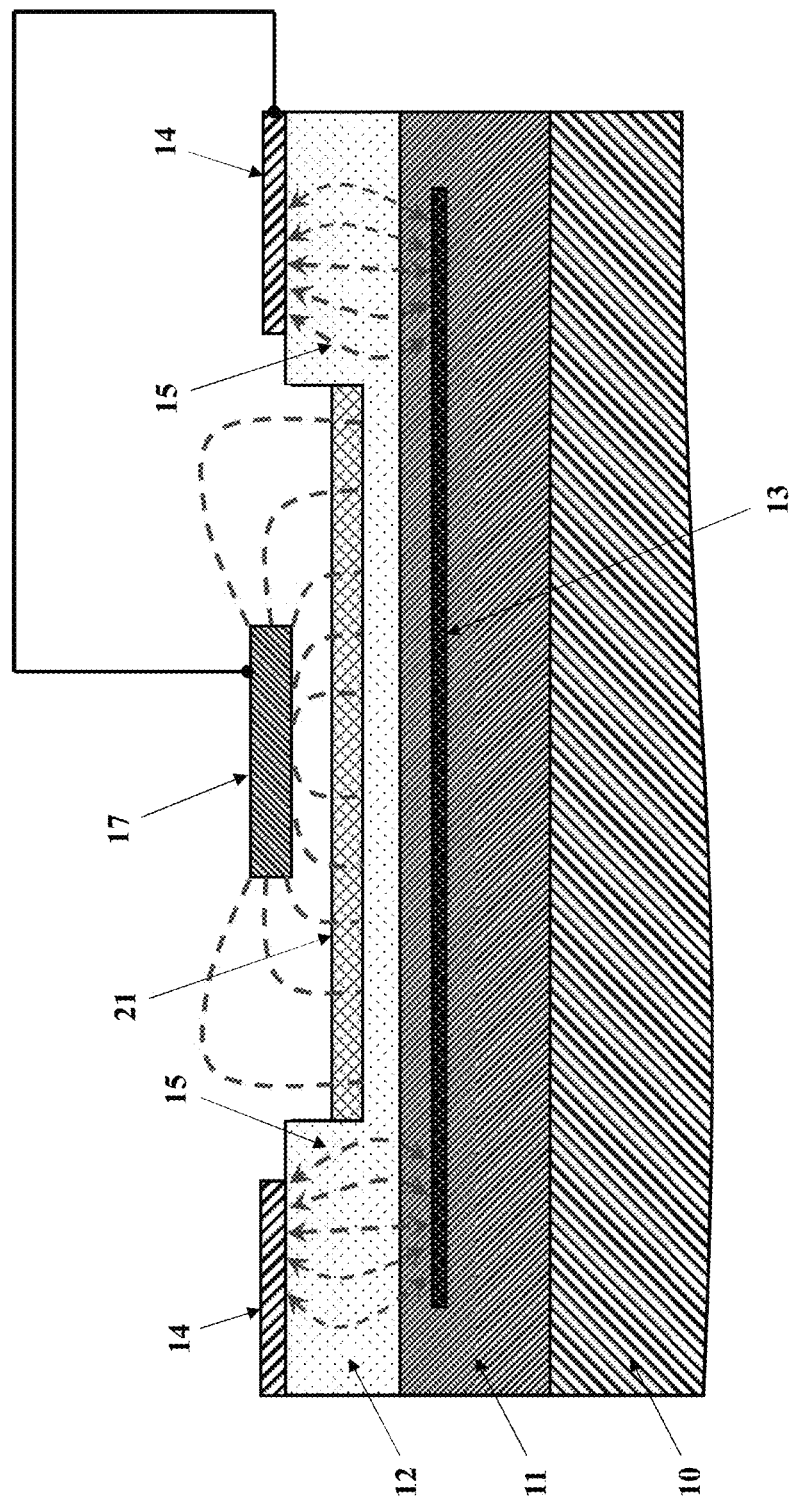
FIG. 9a schematically shows a cross-sectional view of the PC-HEMT configuration of embodiment with a (bio)chemical layer and a mechanically suspended metal gate.

FIG. 9a shows a cross-sectional view of the PC-HEMT configuration of an embodiment with a (bio)chemical layer, comprising:
a multilayer hetero-junction structure made of III-V single-crystalline or polycrystalline semiconductor materials, said structure comprising at least one buffer layer (11) and at least one barrier layer (12), said layers being stacked alternately, and said structure being deposited on a substrate layer (10);
a (bio)chemical layer (21) immobilised on top of said multilayer hetero-junction structure for binding gas molecules;
a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain non-ohmic contacts;
electrical metallizations (14) capacitively-coupled to said 2DEG or 2DHG channel (13) for inducing displacement currents (15), thereby creating non-ohmic source and drain contacts connecting said transistor to an electric circuit; and
a mechanically suspended metal gate electrode (17) placed above said multilayer hetero-junction structure between said non-ohmic source and drain contacts and electrically connected to the source electrical metallization;

wherein:
(i) the thickness (d) of said barrier layer (12) between said source and drain non-ohmic contacts is about 5-9 nm which corresponds to the pseudo-conducting current range between normally-on and normally-off operation mode of the transistor;
(ii) the surface of said barrier layer (12) has a roughness of about 0.2 nm or less; and
(iii) said metal electrode (17) has no physical contact with said barrier layer (12) beneath.

The (bio)chemical layer allows gas molecules to be bound or adsorbed and then detected. This (bio)chemical layer further increases the sensitivity and selectivity of the PC-HEMT-based sensor. The (bio)chemical layer can be made of polymers, redox-active molecules such as phthalocyanines, metalorganic frameworks such as metal porphyrins, for example hemin, biomolecules, for example DNA, receptors, antibodies, proteins, water molecules, for example forming a water vapour layer, such as a boundary surface water layer, oxides, semi conductive layer or catalytic metallic layer. The (bio)chemical layer can be immobilised over either a portion of the contact surface of the barrier layer in the open gate area, or substantially over the entire contact surface of the barrier layer to further improve sensitivity of the PC-HEMT-based sensor.

In a certain embodiment, the (bio)chemical layer may comprise a molecular layer. For example, this could be a layer of molecules that forms dipoles in the presence of a humid gas (or air). In this way, the gas or air can for example be detected by a gate voltage shift. In a specific embodiment, the (bio)chemical layer is a hemin layer.

Figure 9B:
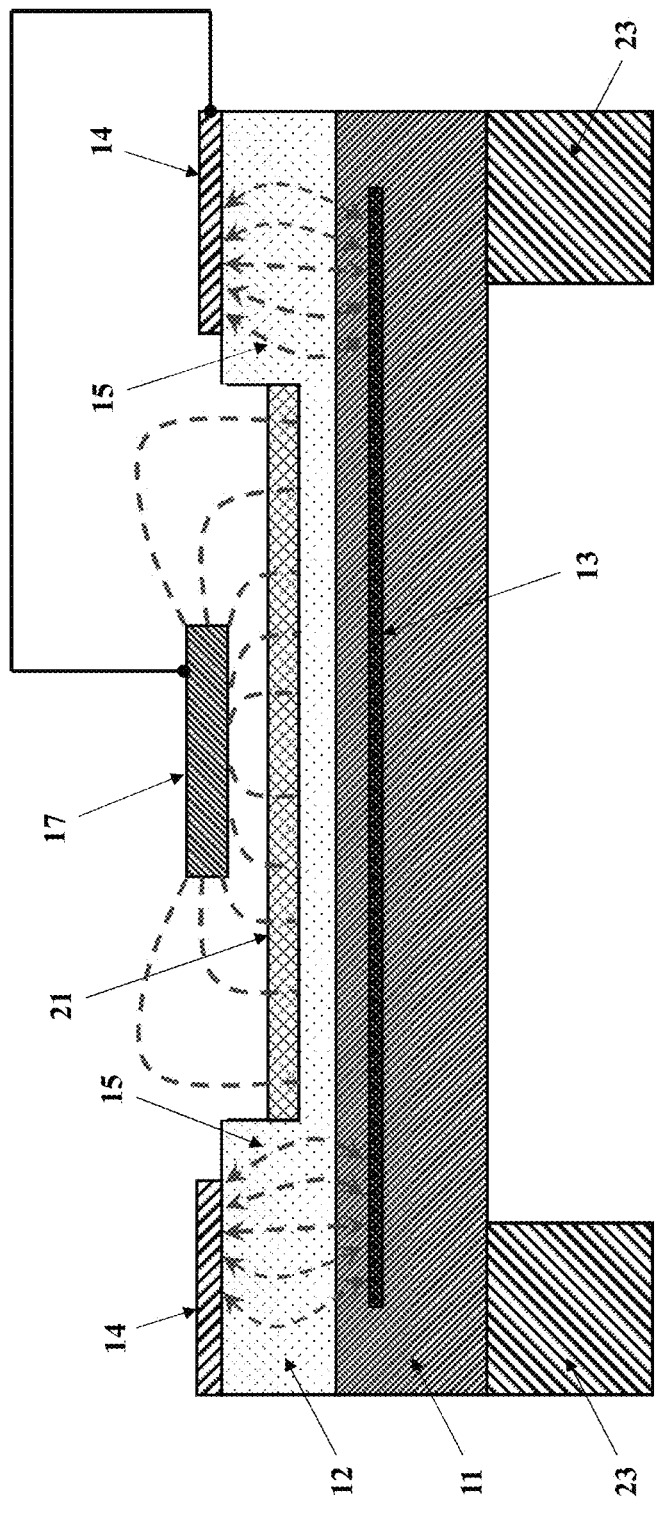
FIG. 9b schematically shows a cross-sectional view of the PC-HEMT configuration of an embodiments with a (bio)chemical layer, a mechanically suspended metal gate and free-standing membranes.

FIG. 9b shows a cross-sectional view of the PC-HEMT configuration of an embodiment with a (bio)chemical layer and free-standing membranes, comprising:
a multilayer hetero-junction structure made of III-V single-crystalline or polycrystalline semiconductor materials, said structure comprising at least one buffer layer (11) and at least one barrier layer (12), said layers being stacked alternately, and said structure being placed on free-standing membranes (23);
a (bio)chemical layer (21) immobilised on top of said multilayer hetero-junction structure for binding gas molecules;
a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain non-ohmic contacts;
electrical metallizations (14) capacitively-coupled to said 2DEG or 2DHG channel (13) for inducing displacement currents (15), thereby creating non-ohmic source and drain contacts connecting said transistor to an electric circuit; and
a mechanically suspended metal gate electrode (17) placed above said multilayer hetero-junction structure between said non-ohmic source and drain contacts and electrically connected to the source electrical metallization;

wherein:
(i) the thickness (d) of said barrier layer (12) between said source and drain non-ohmic contacts is about 5-9 nm which corresponds to the pseudo-conducting current range between normally-on and normally-off operation mode of the transistor;
(ii) the surface of said barrier layer (12) has a roughness of about 0.2 nm or less; and
(iii) said metal electrode (17) has no physical contact with said barrier layer (12) beneath.

Using the above configuration makes is possible to further increase selectivity of the sensor via adding mechanical stress (or mass loading effect) of the (bio)chemical layer as an additional parameter of the PC-HEMT-based sensor. The free-standing membranes (23) are very flexible free-standing columns of substrate made of the same material as the substrate layer (10) in all configurations of the PC-HEMT-based sensor shown above. In a particular embodiment, the free-standing substrate membranes (23) are composed, for example, of sapphire, silicon, silicon carbide, gallium nitride or aluminium nitride, preferably gallium nitride, having thickness of 0.5-2 μm. The free-standing substrate membranes are very sensitive to any tensile/compressive/mechanical stress changes in the (bio)chemical layer during chemisorption of gas or air molecules onto the surface of the multilayer hetero-junction structure. This results in a mass loading effect, which will be discussed below.

In general, mechanical sensors, much like pressure sensors, are based on the measurement of the externally induced strain in the heterostructures. The pyroelectric properties of group-III-nitrides, such as gallium nitride (GaN), allow two mechanisms for strain transduction: piezoelectric and piezoresistive. The direct piezoelectric effect is used for dynamical pressure sensing. For measurements of static pressure, such sensors are not suitable due to some leakage of electric charges under the constant conditions. For static operation, the piezoresistive transduction is more preferable.

Figure 9C:
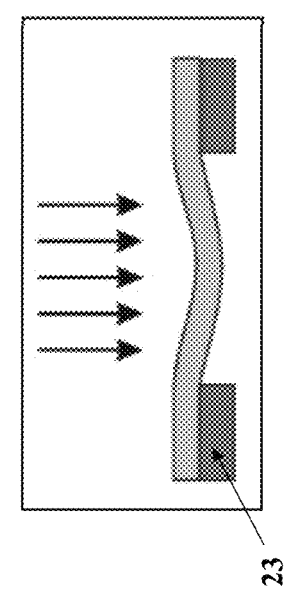
FIG. 9c illustrates a situation when the external pressure (mass effect) is applied on the sensor incorporating transistor of FIG. 9b, and transferred into a changed internal strain caused by bending.

Piezoresistive sensors using wide band gap materials have been previously employed using hexagonal silicon carbide bulk materials for high temperature operation. Piezoresistivity of GaN and AlGaN structures is comparable to silicon carbide. However, piezoresistivity can be further amplified by HEMT structure, as taught by Eickhoff et al (2001). For piezoresistive strain sensing at relatively lower pressures (or pressure differences), diaphragm or membranes should be used, where the external pressure is transferred into a changed internal strain caused by bending, as shown in FIG. 9c. The resulting change in polarization alters the 2DEG channel current which is measured.

Eickhoff et al (2001) conducted the first experiments on GaN/AlGaN heterostructures where the 2DEG channel confined between the upper GaN and AlGaN barrier layer and demonstrated the linear dependence of the 2DEG channel resistivity on the applied strain. Moreover a direct comparison to cubic SiC and a single AlGaN layer clearly demonstrated the superior piezoresistive properties of the latter. From these results, it is clear that the interaction of piezoelectric and piezoresistive properties improves the sensitivity of pressure sensors by using GaN/AlGaN heterostructures confined with the 2DEG channel.

The sensor configuration schematically shown in FIG. 9a involves piezo-electrically coupled, charge and mass sensitive, free-standing GaN membranes, which are prepared, for example, according to U.S. Pat. No. 8,313,968 and offer an elegant and effective solution to achieve both downscaling and an integrated all-electrical low-power sensing-actuation. As mentioned above, GaN exhibits both, piezo- and pyroelectrical properties, which can be functionally combined. Whereas the piezoelectricity enables realisation of an integrated coupling mechanism, the 2DEG additionally delivers a pronounced sensitivity to mechanical stress and charge, which allows the sensor to use the pyroelectric effects. The dynamic change in 2DEG conductivity is also caused by a change in piezoelectric polarisation.

Thus, in order to achieve a maximal possible selectivity of the sensor, a mass loading parameter is added. This can be realised as a "push-pull" auto-oscillator with a certain DC-voltage supply structure. The configuration shown in FIG. 9b offers excellent sensitivity and selectivity for gas, air and volatile organic compounds (VOCs) with a stress (strain) and mass loading effect on the free-standing membrane (23). If negative potential is applied on $V_{GS}$ and positive potential is applied on $V_{DS}$ at the suspended gate (17), then due to electrostatic forces, the suspended gate is mechanically pulled down towards the 2DEG channel (13), which now acts as a "positive" electrode. The resonator is then fine-tuned in such a manner that after moving few nanometres, the negatively charged suspended gate slightly depletes the 2DEG channel. As a result, the attraction force starts diminishing and the suspended gate electrode becomes pushed away (move upwards) from the 2DEG channel. At certain $V_{DS}$-$V_{GS}$ combination, the rapid upward and downward movement of the suspended gate results in a resonance, and high-frequency oscillation takes place. This multi-parametric mechanic push-pull resonance effect makes it possible to measure a mass loading effect of the free-standing membrane with a high sensitivity.

In addition, the RF signal (0.001-20 Hz) used in a dielectric RF spectroscopy can be applied only at $V_{GS}$ or simultaneously at $V_{GS}$ and at $V_{DS}$ of the gate electrode. Due to a shift of the dielectric constant within the (bio)chemical layer after gas/air molecules chemisorption or adsorption, an additional information of RF responsivity of molecular dipoles can be obtained, thereby further increasing the sensor selectivity.

In order to drastically increase the interaction between the gas/air molecules and the RF field, the nanoporous material is added between the gate and the barrier layer surface. If the gas/air molecules diffuse into the pores of the nanoporous material, they will be interacting with the RF field because of their dipole moment, thereby affecting a dielectric constant between the AlGaN barrier layer and the suspended gate. Thus, in another embodiment, the open gate area is at least partially filled with a porous material.

FIG. 10 shows a cross-sectional view of the PC-HEMT configuration of an embodiment with a porous material filling an open gate area, comprising:
a multilayer hetero-junction structure made of III-V single-crystalline or polycrystalline semiconductor materials, said structure comprising at least one buffer layer (11) and at least one barrier layer (12), said layers being stacked alternately, and said structure being deposited on a substrate layer (10) or placed on free-standing membranes;
a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain non-ohmic contacts;
electrical metallizations (14) capacitively-coupled to said 2DEG or 2DHG channel (13) for inducing displacement currents (15), thereby creating non-ohmic source and drain contacts connecting said transistor to an electric circuit; and a mechanically suspended metal gate electrode (17) placed above said multilayer hetero-junction structure between said non-ohmic source and drain contacts and electrically connected to the source electrical metallization;

a porous material (22) filing an open gate area between said source and drain non-ohmic contacts;

wherein:
(i) the thickness (d) of said barrier layer (12) between said source and drain non-ohmic contacts is about 5-9 nm which corresponds to the pseudo-conducting current range between normally-on and normally-off operation mode of the transistor;
(ii) the surface of said barrier layer (12) has a roughness of about 0.2 nm or less; and
(iii) said metal electrode (17) has no physical contact with said barrier layer (12) beneath.

As shown in FIG. 10, the open gate area is at least partially filled with a porous material (22), and the porous material may be applied over the surface of the barrier layer substantially filling the entire open gate area. The porous material can be any nanoporous gate dielectric, for example, a nanoporous insulation sheet (NPS) of adjustable 1-20 nm pore size. Gas or air molecules will diffuse into the pores, enter the open gate area and interact with the electric field of the transistor altering the electric current in the 2DEG channel and $V_{GS}$, as described above. This will result in a change of permittivity and susceptibility. Since each molecule is selectively oscillated in a single pore, a selective detection becomes possible. The AC electronic readout can be combined with the standing-wave interferometry (DC or LED pulsed), thereby adding another selective interaction to the resonance. When a dielectric nanoporous elastomer is used as a gate dielectric, a mechanical resonator can be generated, resulting in the RF resonance.

In another aspect of the present disclosure, FIG. 11 schematically shows a microelectronic sensor comprising the following components:

the PC-HEMT of an embodiment, or an array thereof (100), printed on a flexible printed circuit board (PCB) (108), wherein each one of said transistors is connected via electrical metallizations (14) to its dedicated electrical contact line (103) printed on said PCB (108);

one common metal gate electrode (110) placed on said PC-HEMT or an array thereof (100), and electrically connected to a contact surface or to a contact wire;

a voltage source (104) connected to said electrical contact lines (103) via an electric circuit (102) for supplying electric current to said transistors;

an integrated or CMOS current amplifier (105) connected to said voltage source (104) for amplification of an electric current obtained from said transistors;

an analogue-to-digital converter (ADC) with in-built digital input/output card (106) connected to said current amplifier (105) for outputting the converted signal to a user interface; and a connection module (107) for connecting the sensor to the user interface.

All the above components of the sensor can be external or built in the transistor. Each PC-HEMT of this sensor is fabricated on the substrate comprising 6-inch silicon wafers, the GaN buffer layer and the ultrathin grown AlGaN barrier layer, as described above. The AlGaN/GaN hetero-junction parameters used in this particular transistor were optimised for the ultrathin AlGaN barrier layer as follows: 3.5 nm SiN cap on top of the barrier layer, 6 nm Al0.25Ga0.75N and 2 µm GaN buffer layer deposited on the Si wafer substrate. All the measurements further exemplified with this sensor were carried out on the fabricated samples without any additional surface treatment after ion implantation based 2DEG patterning step.

The fabricated sensor is glued on the flexible fibro-plastic PCB (108), and its wire bond connectors are protected with epoxy-based glob-top (109). The voltage source (104) can be any suitable and commercially available battery of the Li-ion type or any energy harvester with AC-DC or DC-DC converters. The ADC card (106) is any suitable analogue-to-digital converter card that can be purchased, for example, from National Instruments® or LabJack®. The current amplifier (105) can be any commercially available femto-ampere amplifier, for example SRS® SR570, DLPVA-100-F-S, FEMTO® current amplifier DDPCA-300 or Texas Instruments® INA826EVM.

In a particular embodiment, the sensor is powered by a battery, such as an AA-battery. The connection module (107) can be an USB, a NFC or Bluetooth. There are two possibilities for the sensor setup operation including either a differential voltage amplifier connected in parallel, for example SRS® SR560, or a current amplifier connected in-line, for example a femtoamplifier SRS® SR570. The SR560 setup allows the operation in high input impedance mode using the voltage divider resistance R. The relatively high SR560 input resistance of 100 MΩ is good for detection of very small charges without big leakages.

Another setup includes a current amplifier that operates directly with current flowing via the 2DEG channel of the PC-HEMT into the amplifier with small input resistance of 1MΩ at gain higher than $10^4$ and only 11 at gains lower than 200. Since the current amplifier in this case is switched off, the usage of voltage divider R is not necessary unless the voltage of 1.6V from the AA-element is too high. Thus, this setup directly amplifies the electric current modulation in the 2DEG channel originated from an external body charges. All readout components are battery powered to avoid ground loop parasitic current.

In a further embodiment, the sensor shown in FIG. 12 contains a common suspended metal gate electrode (110), which has no physical contact with the PC-HEMT or array thereof (100). The metal gate electrode (110) in this case is placed directly above the PC-HEMT or array thereof (100), at the height of 10-100 nm. This configuration prevents any electrical leakage normally occurring at the metal gate/barrier layer interface.

FIG. 13 shows the sensor where either the mechanically suspended metal gate electrode or the metal gate electrode placed in contact with the transistors is discharged via the connection to the source electrode. The connection can be high-ohmic and can be established via capacitor to prevent the strong signal decay.

In some embodiments, the PC-HEMT sensor may be integrated in a smart watch, in a smartphone or in any other available personal gadget, including but not limited to a bracelet, a ring, a pen or an earring. It can be also integrated in any home appliance, or installed in-door or out-door. The in-built PC-HEMT sensor is capable of sensing the signals and transmitting them either to a smartphone, smartwatch or to any other available personal gadget or mobile device, to a desktop computer, server, remote storage, internet storage or directly to an air quality monitoring network cloud. The air quality monitoring can be continuously carried out when the sensor is switched on. The relevant air quality data recorded is then transmitted to an air quality monitoring network cloud and will be available for further processing.

In a certain aspect, an air quality monitoring device of the present application contains an integrated PC-HEMT sensor comprising the following components:

the PC-HEMT of an embodiment, or an array thereof, wherein each one of said transistors is connected to its dedicated electrical contact line;

a battery connected to said electrical contact lines via an electric circuit for supplying electric current to said transistors;

an integrated or CMOS current amplifier connected to said battery for amplification of an electric current obtained from said transistors;

an analogue-to-digital converter (ADC) with in-built digital input/output card connected to said current amplifier for wirelessly outputting the converted signal to a smartphone or to an authentication cloud;

a wireless connection module for wireless connection of said air quality monitoring device to a smartphone or to an air quality monitoring network cloud.

In a specific embodiment, the wireless connection module can be a short-range Bluetooth or NFC providing wireless communication between the wearable device and a smartphone for up to 20 m. If this module is WiFi, the connection can be established for up to 200 nm, while GSM allows the worldwide communication to an air quality monitoring network cloud.

In some embodiments, the device of the present application can be used for portable long-time-operation solution within a cloud-based network. Since the device is intended for continuous use, it should have a very small power consumption saving the battery life for a prolong usage. This is one of the major reasons to use the non-ohmic high-resistive contacts connecting the PC-HEMT sensor to an electric circuit. The non-ohmic contacts actually limit an electric current flowing through the 2DEG channel by having an electrical resistance 3-4 times higher than the resistance of the 2DEG-channel, thereby reducing electrical power consumption without sacrificing sensitivity and functionality of the sensor. Thus, the use of non-ohmic contacts in some embodiments of the PC-HEMT sensor of the present application is a hardware solution allowing minimising the power consumption of the device. In another embodiment, the power consumption of the device can be minimised using a software algorithm managing the necessary recording time of the sensor and a battery saver mode, which limits the background data and switches the wireless connection only when it is needed.

As mentioned above, the PC-HEMT sensor may also be integrated within the smartphone or smart-watch. Optionally, the sensor may be placed inside the smartphone or personal gadget. It can be connected to the metallic chassis or to the capacitive sensitive display elements of the smartphone transducing an electrical charge to the sensor. The PC-HEMT sensor may also be installed (glued or attached) on any solid surface, such as indoor walls or ceilings or on any outdoor surface. It can be also used in a construction and automotive sector.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

The invention claimed is:

1. A microelectronic sensor for air quality monitoring comprising:
    1) an array of open-gate pseudo-conductive high-electron mobility transistors printed on a flexible printed circuit board (PCB), and connected to their dedicated electrical contact lines printed on said PCB;
    2) one common metal gate electrode electrically connected to a contact surface or to a contact wire and placed over said transistors at a height of 10-100 nm, without physical contact with said transistors;
    3) a voltage source connected to said electrical contact lines via an electric circuit for supplying electric current to said transistors;
    4) an integrated or complementary metal-oxide-semiconductor (CMOS) current amplifier connected to said voltage source for amplification of an electric current obtained from said transistors;
    5) an analogue-to-digital converter (ADC) with in-built digital input/output card connected to said current amplifier for outputting a converted signal to an external memory; and
    6) a connection module for connecting the microelectronic sensor to the external memory;
    characterised in that each one of said transistors comprises:
    (a) a multilayer hetero-junction structure made of gallium nitride (GaN) and aluminium gallium nitride (AlGaN) single-crystalline or polycrystalline semiconductor materials, and deposited on a substrate layer or placed on free-standing membranes; said structure comprising at least one buffer layer and at least one barrier layer, said layers being stacked alternately;
    (b) a conducting channel comprising a two-dimensional electron gas (2DEG) or a two-dimensional hole gas (2DHG), formed at an interface between said buffer layer and said barrier layer, and upon applying a bias to said transistor, becoming capable of providing electron or hole current, respectively, in said transistor between source and drain contacts;
    c) source and drain contacts connected to said 2DEG or 2DHG conducting channel and to electrical metallizations for connecting said transistor to an electric circuit; and
    d) an open gate area between said source and drain contacts;
    said transistor is characterised in that a thickness of the top layer of said heterojunction structure in the open gate area is 5-9 nanometres (nm) and a surface of said top layer has a roughness of 0.2 nm or less, wherein the combination of said thickness and said roughness of the top layer is suitable for creating a quantum electronic effect of operating said 2DEG or 2DHG channel simultaneously in both normally-on and normally-off operation modes of the channel, thereby making said transistor suitable for conducting electric current through said channel in a quantum well between normally-on and normally-off operation modes of the transistor.

2. The microelectronic sensor of claim 1, wherein said multilayer hetero-junction structure comprises: (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have N-face polarity, thus forming a two-dimensional electron gas (2DEG) conducting channel in the top GaN layer, close to the interface with said AlGaN barrier layer, and said structure further comprises an additional AlN or AlGaN layer having a high Al content and thickness of 1 nm or less, in the top GaN buffer layer above the 2DEG channel.

3. The microelectronic sensor of claim 1, wherein each one of said transistors further comprises a metal gate electrode electrically connected to the source electrical metallization and placed directly on the recessed top layer between said source and drain non-ohmic contacts, or mechanically suspended above the recessed top layer between said non-ohmic source and drain contacts without any physical contact with said recessed top layer.

4. The microelectronic sensor of claim 1, wherein each one of said transistors further comprises a porous material filling said open gate area between said source and drain non-ohmic contacts.

5. The microelectronic sensor of claim 1, wherein each one of said transistors further comprises a biochemical layer immobilised on top of said multilayer hetero-junction structure for binding gas molecules.

6. The transistor of claim 1, wherein said source and drain contacts are ohmic.

7. The transistor of claim 1, wherein said electrical metallizations are capacitively coupled to said 2DEG or 2DHG conducting channel for inducing displacement currents, thus resulting in said source and drain contacts being non-ohmic.

8. The microelectronic sensor of claim 1, wherein each one of said transistors further comprises a dielectric layer deposited on top of said multilayer hetero-junction structure.

9. The microelectronic sensor of claim 8, wherein said dielectric layer comprises SiO—SiN—SiO ("ONO") stack or SiN—SiO—SiN ("NON") stack of 100-100-100 nm thickness.

10. The microelectronic sensor of claim 1, wherein each one of said transistors further comprises a gas permeable membrane mounted on top of the transistor and covering said open gate area between said source and drain non-ohmic contacts.

11. The microelectronic sensor of claim 1, wherein said substrate layer of each one of said transistors comprises sapphire, silicon, silicon carbide, gallium nitride or aluminium nitride.

12. The microelectronic sensor of claim 1, wherein the thickness of said recessed top layer in said open gate area of each one of said transistors is 6-7 nm.

13. The microelectronic sensor of claim 12, wherein the thickness of said recessed top layer in said open gate area is 6.2 nm to 6.4 nm.

14. The microelectronic sensor of claim 13, wherein the surface roughness of said recessed top layer in said open gate area is 0.1 nm or less, or 0.05 nm or less.

15. The microelectronic sensor of claim 1, wherein the free-standing membranes of each one of said transistors, on which the multilayer hetero-junction structure is placed, are free-standing columns of substrate composed of sapphire, silicon, silicon carbide, gallium nitride or aluminium nitride.

16. The microelectronic sensor of claim 15, wherein said substrate is gallium nitride (GaN) having thickness of 0.5-2 µm.

17. The microelectronic sensor of claim 1, wherein said external memory is included in a smart-phone, smartwatch, any other available personal gadget or mobile device, a desktop computer, server, remote storage, internet storage, indoor, outdoor display, or an air quality monitoring network cloud.

18. A method for air quality monitoring comprising:
  1) installing the microelectronic sensor of claim 1 indoor or outdoor, or attaching said microelectronic sensor to a user's body in a form of a wearable device or gadget;
  2) continuously recording electrical signals received from said microelectronic sensor in a form of a source-drain electric current of the transistors over time (defined as $I_{DS}$ dynamics);
  3) continuously transmitting the recorded signals from said microelectronic sensor to the external memory for further processing; and
  4) processing the transmitted signals in the external memory, correlating said $I_{DS}$ dynamics with a pre-calibrated air quality data and extracting the air quality data from said signals in a readable format, thereby continuously monitoring the air quality.

19. The method of claim 18, further comprising the step of discharging and fine tuning microelectronic sensor gain by changing voltage ($V_{DS}$) between said source and drain non-ohmic contacts of the transistors.

* * * * *